United States Patent
Rahmo

(10) Patent No.: US 11,345,886 B2
(45) Date of Patent: May 31, 2022

(54) SMALL MOBILE STEM CELLS (SMS) AND USES THEREOF

(71) Applicant: SMSBIOTECH, INC., Irvine, CA (US)

(72) Inventor: Abdulkader Rahmo, Glendale, CA (US)

(73) Assignee: SMSBIOTECH, INC., Irvine, CA (US)

( * ) Notice: Subject to any disclaimer, the term of this patent is extended or adjusted under 35 U.S.C. 154(b) by 902 days.

(21) Appl. No.: 16/039,280

(22) Filed: Jul. 18, 2018

(65) Prior Publication Data

US 2019/0010448 A1 Jan. 10, 2019

Related U.S. Application Data

(63) Continuation of application No. 14/896,142, filed as application No. PCT/US2014/041598 on Jun. 9, 2014, now Pat. No. 10,041,037.

(60) Provisional application No. 61/833,467, filed on Jun. 11, 2013.

(51) Int. Cl.
| | |
|---|---|
| *C12N 5/071* | (2010.01) |
| *A61K 35/28* | (2015.01) |
| *C12N 5/0775* | (2010.01) |
| *C07K 14/47* | (2006.01) |
| *G01N 33/50* | (2006.01) |

(52) U.S. Cl.
CPC ............ *C12N 5/0602* (2013.01); *A61K 35/28* (2013.01); *C07K 14/47* (2013.01); *C12N 5/0665* (2013.01); *G01N 33/5073* (2013.01)

(58) Field of Classification Search
CPC .................................................. C12N 5/0602
See application file for complete search history.

(56) References Cited

U.S. PATENT DOCUMENTS

2015/0093447 A1 4/2015 O'Neil

OTHER PUBLICATIONS

Sun et al. Cancer Letters, 2010, 296:178-185.*
Choi et al. Korean J Reprod Med, 2010, 37(2):99-113.*
Lee et al., BBRC, 2006, 341:882-888).*
Zuba-Surma et al., Cytomestry, 2009, 75(1):1-19 as printed.*
International Preliminary Report on Patentability dated Dec. 23, 2015, received in corresponding International Patent Application No. PCT/US2014/041598.
Rahmo, A. et al. "Introducing a Novel Human Stem Cell with Exceptional Characteristic." J. of Life Sciences and Technologies, Mar. 2013, vol. 1, No. 1, p. 56-61.
Rahmo, Abdulkader. "Introducing a Novel Human Stem Cell with Exceptional Characteristics: Small, Mobile Stem Cells (SMS)." 3rd International Conference on Life Science and Technology Dubai AUE Management (ICLST 2013). Jan. 19-20, 2013.
Sokurenko L.M. «Morfologicheskie issledovaniya deistviya lekarstvennykh veschestv v toksikologii», Farmakoterapiya, 2012, No. 5(161), p. 62-68.
Thomson et al. PNAS USA, 92, 7844-7848, 1995.
Wojakowski et al. J Cardiovasc Trans Res (2011) 4:138-144.
Divya, et al. Umbilical cord blood-derived mesenchymal stem cells consist of a unique population of progenitors co-expressing mesenchymal stem cell and neuronal markers capable of instantaneous neuronal differentiation. *Stem Cell Res Ther* 3, 57 (2012).
Horwitz, et al. Mesenchymal stromal cells. *Curr Opin Hematol.* 13, 6 (2006).

* cited by examiner

*Primary Examiner* — Bin Shen
(74) *Attorney, Agent, or Firm* — Knobbe, Martens, Olson & Bear LLP

(57) ABSTRACT

The presently disclosed subject matter relates, in general, to the identification, isolation, and use of a population of stem cells isolated from umbilical cord blood, peripheral blood and/or other sources and that are referred to herein as Small Mobile Stem cells (short: SMS). More particularly, the presently disclosed subject matter relates to isolating said SMS stem cells and employing the same, optionally after in vitro manipulation, to treat tissue and/or organ damage in a subject in need thereof.

5 Claims, 44 Drawing Sheets

SMALL MOBILE STEM CELLS (SMS) AND USES THEREOF

CROSS-REFERENCE TO RELATED APPLICATIONS

This application is a continuation of U.S. patent application Ser. No. 14/896,142, filed Dec. 4, 2015, which is a U.S. National Phase Application of PCT International Application Number PCT/US2014/041598, filed on Jun. 9, 2014, designating the United States of America and published in the English language, which is an International Application of and claims the benefit of priority to U.S. Provisional Application No. 61/833,467, filed on Jun. 11, 2013. The disclosures of the above-referenced applications are hereby expressly incorporated by reference herein in their entireties.

FIELD OF THE INVENTION

The presently disclosed subject matter relates, in general, to the identification, isolation, and use of a population of stem cells isolated from one or more sources, including but not limited to umbilical cord blood, peripheral blood, bone marrow, solid tissues such as placenta, liver, heart, brain, kidney and gastro intestinal tract, and that are referred to herein as Small Mobile Stem cells (SMS). More particularly, the presently disclosed subject matter relates to isolating said SMS stem cells and employing the same, optionally after in vitro manipulation, to treat tissue and/or organ damage in a subject in need thereof.

BACKGROUND OF THE INVENTION

The use of stem cells and stem cell derivatives is currently of great interest to medical research, particularly for the prospects of providing reagents for treating tissue damaged by various causes such as genetic disorders, injuries, and/or disease processes. In theory, stem cells, capable of asymmetric division; replenishing them self and providing various differentiated cell types could replace any damaged cells and tissues of an organism of choice. This process of regeneration is inherently present, to various extents, in all living multicellular organisms. Human organs however vary greatly in their potential for regeneration and repair. Many vital organs such as the heart and the brain show little capacity for repair after injury.

A lot of effort was concentrated at isolating and identifying human stem cells from a number of different tissues for use in regenerative medicine. And since bone marrow transplants have been successfully performed for decades, such efforts were concentrated initially on identifying stem cells in bone marrow. U.S. Pat. No. 5,750,397 discloses the isolation and growth of human hematopoietic stem cells that are reported to be capable of differentiating into lymphoid, erythroid, and myelomonocytic lineages. U.S. Pat. No. 5,736,396 discloses methods for lineage-directed differentiation of isolated human mesenchymal stem cells under the influence of appropriate growth and/or differentiation factors. The derived cells can then be introduced into a host for mesenchymal tissue regeneration or repair.

Another area of interest was the use of embryonic stem (ES) cells. These stem cells have been shown in mice to have the potential to differentiate into all the different cell types of the animal. Mouse ES cells are derived from cells of the inner cell mass of early mouse embryos at the blastocyst stage, and other pluripotent and/or totipotent cells have been isolated from germinal tissue (e.g., primordial germ cells; PGCs). Unfortunately, the development of human ES (hES) cells was not as successful.

In addition to the ethical controversy inherent to the use of human ES cells, significant other challenges face the use of ES cells or other pluripotent cells for regenerative therapy. The control of growth and differentiation of the cells into the particular cell type required for treatment of a subject is difficult. There have been several reports of the effect of growth factors on the differentiation of ES cells. For example, Schuldiner et al. report the effects of eight growth factors on the differentiation of cells into different cell types from hES cells (Schuldiner et al. (2000) 97 Proc Natl Acad Sci USA 11307-11312). As disclosed therein, after initiating differentiation through embryoid body-like formation, the cells were cultured in the presence of bFGF, TGFβ1, activin-A, BMP-4, HGF, EGF, βNGF, or retinoic acid. Each growth factor had a unique effect on the differentiation pathway, but none of the growth factors directed differentiation exclusively to one cell type. Also the current strategies for isolating ES cell lines, particularly human ES cell lines, preclude isolating the cells from a subject and reintroducing them into the same subject (autologous transfer). The use of a subject's own cells would obviate the need for adjunct immunosuppressive therapy, maintaining thereby full competency of the immune system.

Adult human stem cells such as MSCs have been shown to have the potential to differentiate into several lineages including bone (Haynesworth et al. (1992) 13 Bone 81-88), cartilage (Mackay et al. (1998) 4 Tissue Eng 415-28; Yoo et al. (1998) 80 J Bone Joint Surg Am 1745-57), adipose tissue (Pittenger et al. (2000) 251 Curr Top MicrobiolImmunol 3-11), tendon (Young et al. (1998) 16 J Orthop Res 406-13), muscle, and stroma (Caplan et al. (2001) 7 Trends Mol Med 259-64).

Another population of cells, multipotent adult progenitor cells (MAP Cs), has also been purified from bone marrow (BM; Reyes et al. (2001) 98 Blood 2615-2625; Reyes & Verfaillie (2001) 938 Ann NY Acad Sci 231-235). These cells have been shown to be capable of expansion in vitro for more than 100 population doublings. MAPCs have also been shown to be able to differentiate under defined culture conditions into various mesenchymal cell types (e.g., osteoblasts, chondroblasts, adipocytes, and skeletal myoblasts), endothelium, neuroectoderm cells, and more recently, into hepatocytes (Schwartz et al. (2000) 109 J Clin Invest 1291-1302).

In vivo experiments in humans demonstrated that transplantation of CD34+ peripheral blood (PB) stem cells led to the appearance of donor-derived hepatocytes (Korbling et al. (2002) 346 N Engl J Med 738-746), epithelial cells (Korbling et al. (2002) 346 N Engl J Med 738-746), and neurons (Hao et al. (2003) 12 J Hematother Stem Cell Res 23-32). Additionally, human BM-derived cells have been shown to contribute to the regeneration of infarcted myocardium (Stamm et al. (2003) 361 Lancet 45-46). Currently Adult stem cells such as mesenchymal stem cells are widely investigated in clinical trials for a variety of diseases (Ali et al. (2012) 2 (1) Stem Cell Discovery 15-23).

Recently a population of very small stem cells has been isolated using FACS cell sorting. These were named very small embryonic like stem cell (VSEL). This is a rare cell population that possess very primitive morphology and express pluripotent stem cell markers (e.g., Oct4, Nanog, and SSEA-4) as well as the surface phenotype Seal+/CD133+Lin-CD 45− in mice/humans. VSELs can be mobilized into peripheral blood following acute myocardial infarction (Kucia et al. (2008) 26 Stem Cells 2083-2092), and is reported to improve heart function and alleviate cardiac remodeling (Dawn et al. (2008) 26 Stem cells 1646-55, Zuba-Surma et al. (2011) 15 J Cell Mol Med 1319-28).

Attempts to culture these cells (VSEL) were unsuccessful, which led some researchers to question their very presence in human (Danova et al. (2012) 7 PLoS One e34899). Other researchers such as Gu et al. (2013) found also that it is very difficult expand or culture human VSELs in vitro using general culture conditions. Thus it is not clear yet whether these cells are merely developmental remnants found in the adult tissue that cannot be harnessed effectively for regeneration or that they represent real stem cell population suitable for regenerative medicine.

Generally obtaining Adult stem cells from tissues other than bone marrow continues to be difficult; especially for the case of providing sufficient cells for autologous transfer. Nonautologous transfer of cells implanting stem cells to others is on the other hand prone to problems associated with an immune rejection reaction and would require an adjunct immune suppressive therapy. Ex vivo culturing of adult stem cells is used as an alternative for providing sufficient cells. However adult stem cells are relatively sensitive to incubation conditions and if successfully cultured require strict control of these conditions (Bhattacharya et al., (2009) Frontiers of Cord Blood Science, Springer-Verlag London Limited).

The concept of transdifferentiation of adult tissue-specific stem cells is a topic of extensive disagreement within the scientific and medical communities (see e.g., Lemischka (2002) 30 Exp Hematol 848-852; Holden & Vogel (2002) 296 Science 2126-2129). Studies attempting to reproduce results suggesting transdifferentiation with neural stem cells have been unsuccessful (Castro et al. (2002) 297 Science 1299). It has also been shown that the hematopoietic stem/progenitor cells (HSPC) found in muscle tissue originate in the BM (McKinney-Freeman et al. (2002) 99 Proc Natl Acad Sci USA 1341-1346; Geiger et al. 100 Blood 721-723; Kawada & Ogawa (2001) 98 Blood 2008-2013). Additionally, studies with chimeric animals involving the transplantation of single HPCs into lethally irradiated mice demonstrated that transdifferentiation and/or plasticity of circulating HPSC and/or their progeny, if it occurs at all, is an extremely rare event (Wagers et al. (2002) 297 Science 2256-2259).

The clinical experimental use of stem cells is based mainly on providing individual cells that are more or less differentiated. The success of engraftment is dependent on introduced cells homing to the correct location and positioning there in a correct manner that would create a functional tissue (Chute et al (2006) 13(6) Curr Opin Hematol. 399-406). Reliance on cell therapy, as opposed to tissue therapy, is mainly due to the difficulty of inducing cells to structure tissue typical macrostructures in vitro. Many of the newly investigated and introduced innovations are targeting this problem by applying natural or artificial scaffolds or various other means, including the use of extracellular matrix derived from other cells and tissues.

There continues to be a need in cell therapy for new approaches to generate populations of transplantable cells suitable for a variety of applications. These cells should be easy to isolate, cheap to maintain, and provide efficient ex vivo proliferation and differentiation. On the other hand there is the need for stem cells capable of establishing in vitro pre-prepared tissue like structures, engineered preferably of autologous components.

SUMMARY OF THE INVENTION

Disclosed herein, in certain embodiments, is a newly isolated human adult stem cell: Small Mobile Stem cell (SMS). In various embodiments, this cell line is isolated from umbilical cord blood, peripheral blood, bone marrow, solid tissues such as placenta, liver, heart, brain, kidney, or gastro intestinal tract.

The SMS cells described herein are technically stem cells (i.e., undifferentiated cells of a multicellular organism that are capable of giving rise to indefinitely more cells of the same type, and from which certain other kinds of cells arise by differentiation) but have significant difference. Specifically, SMS cells do not merely regenerate lost cells but rather have the ability to reconstruct a whole complex set up of tissue-like structures in the absence of special stimuli or supporting agents.

In specific embodiments, the SMS cells are successfully cultured for at least 3 months using the same growth medium without a serum, e.g., Fetal Bovine Serum (FBS). In these embodiments, the cells are cultured without serum with no significant effect on the proliferation potential, shape or appearance of the cells.

In contrast to cells which affect the positioning of other cells by remotely secreting signal substances, the SMS cells described herein and cells derived therefrom, displace the position of cells by physically carrying them.

In various embodiments, the SMS cell line exhibits exceptional characteristics, including but not limited to: robust growth in standard medium for more than 30 passages, resistance to adverse conditions, growth in absence of serum, formation of cell culture multilayer, capacity for differentiation into different specialized cells, which makes it most ideal for autologous cell therapy. In some embodiments, the SMS cell lines also excrete heavily extra cellular matrix (ECM) providing therefore an important source of this valuable substances.

Production of ECM, makes SMS cell type a candidate supportive cell for productive coculturing with other cells. SMS cell line demonstrates further an extraordinary ability for forming complex multicellular macrostructures in vitro. These macrostructures resemble those observed in human and animal tissues and organs, making it a potential riche source for autologous tissue replacement.

In various embodiments, provided herein are isolated cell line comprising Small Mobile Stem cells (SMS) and uses thereof.

In some embodiments, the SMS cells have a size of less that about 10 µm, or less that about 8 µm, or less that about 6 µm, or between about 3 µm to about 6 µm, or between about 4 µm to about 6 µm, or between about 4.5 µm to about 6.5 µm.

The SMS cells disclosed herein maintain a geometrically defined characteristic for the nucleus, allowing them to be differentiated from other cells without the need for one or more probes.

In various embodiments, the SMS cells exhibit a translucent-like cytoplasm. In some embodiments the SMS cells also exhibit a circular nucleus (2.5-3.5 µm) that includes a centrally located very small circle (1-1.5 µm) of different light contrast. In specific embodiments, the circular nucleus is about 2.5-3.5 µm and includes a centrally located very small circle with a size of 1-1.5 µm and having a different light contrast. In these embodiments, depending on focusing plane, the minute circle appears darker or lighter. These contours of the cell bear resemblance to the shape of a human "Iris" and, for cells that remain undifferentiated, are stable throughout cell culture.

In some embodiments, the undifferentiated SMS cells do not stain with standard staining techniques. Non-limiting examples of standard staining techniques include Wright's stain, Coomassie blue, Neutral red, Safranin, Silver staining, Masson's trichrome, Amido black, Toluidine blue, methylene blue, PAS staining, Trypan-blue, and Haematoxylin. In other embodiments, the cell that remains undifferentiated is stable through cell culture.

In various embodiments, the speed of moving SMS cells reaches about 1.5 µm/sec; which is about three times faster than the fastest reported cell of human origin: the neutrophils (a maximum speed of 0.5 µm/sec). See, e.g., Stossel, T. P. "The E. Donnall Thomas Lecture, 1993. The machinery of blood cell movements", Blood 84.2 (1994):367. In some embodiments, the high mobility speed of the SMS cells is greater than about 0.5 µm/sec. In specific embodiments, the high mobility speed is about 1.5 µm/sec.

In some embodiments, the SMS cells are expressive of extracellular matrices m standard media, including but not limited to DMEM low glucose, DMEM high glucose, with or without Hepes and/or serum.

In various embodiments, the SMS sells are capable of forming an organized extracellular matrix (ECM). In these embodiments, the formation of the organized ECM makes the cells amenable for practical applications, including but not limited to industrial applications as well as medical applications. The ability of the SMS cells to produce ECMs is unique to these cells and allows for the production of a protein.

The SMS cells disclosed herein are sensitive to environmental changes while being resistant to adverse conditions. For example, the SMS cells are sensitive to media compositions conducive to differentiation, as well as changes to PH and temperature. These same cells are resistant to adverse conditions that cause death to other human cells including but not limited to elevated or reduced temperatures, PH, ionic strength, freezing and thawing in growth medium. For example, various embodiments of the SMS cells described herein can be frozen and then thawed without the need for a protectant.

In some embodiments, the media is DMEM low glucose or DMEA high glucose, optionally with Hepes or serum. In other embodiments, the environmental change is a media composition conducive to differentiation, a change to the pH, an elevated temperature or a reduced temperature and the adverse condition that causes death to other human cells is freezing and thawing in a growth medium, ionic strength, elevated or reduced temperature, or pH. In specific embodiments, the elevated temperature is about 90° C. and the reduced temperature is less than about −20° C. In other specific embodiments, the pH is between about 6 to 9.

Various embodiments of the SMS cells are robust and highly proliferative in standard media. For example, a single SMS cell line maintains a state of continuous growth for at least one 1 year, at least 2 years, at least 3 years, at least 4 years, or between 1-5 years, between 1-4 years, or between 2-3 years.

In various embodiments, the SMS cell lines can be grown in a basal medium without serum or special additives, including but not limited to growth factors. These cells are also responsive to differentiation inductive media efficient for differentiation of other types of cells.

In various embodiments, provided herein is an isolated cell line comprising: Small Mobile Stem cells (SMS), wherein the SMS: (i) have a size of between about 4.5 to about 5.5 mm; (ii) have a regular characteristic nuclear shape and a largely translucent cytoplasm; (iii) have an exceptionally high mobility speed; (iv) are expressive of extracellular matrix in a standard media; (v) form an organized ECM layer and cellular multilayers; (vi) are sensitive to environmental changes and resistant to adverse conditions that cause death to other human cells; (vii) are robust and proliferative in standard media for more than 30 passages; (viii) can be grown in absence of serum and special additives; and (ix) are responsive to common differentiation inductive media.

In some embodiments, the regular characteristic nuclear shape includes a circular nucleus. In specific embodiments, the circular nucleus is about 2.5-3.5 µm and includes a centrally located circle of about 1-1.5 µm.

In various embodiments, the original cells are isolated from umbilical cord blood, peripheral blood, bone marrow, or a solid tissue. Specific non-limiting examples of solid tissue useful in the invention described herein are placenta, liver, heart, brain, kidney or gastro intestinal tract.

In some embodiments, the SMS cells form a strong attachment to plastic and a poor attachment to normal glass.

In other embodiments, the SMS cells readily form multifunctional complex assemblies of cells.

In some specific embodiments, the SMS cells are successfully cultured in an osteogenic differentiation medium and assemble into complex structures.

In some specific embodiments, the SMS cells act as Peelers (i.e., peel a rectangular portion of the ECM membrane). In these embodiments, the SMS derived cells initially cut the connective membrane to variable distance and then cut at the two ends at fixed angles to the prior incision for extended lengths. In these embodiments, each of the duplicate membrane incisions continue to proceed parallel in an equidistant mode resulting in a long stretch of rectangular membrane with constant diameter.

In other specific embodiments, the SMS derived cells act as coaters (i.e., are generators of flat membranes, are surface crawlers and appear to be multi-surface feeders). In these embodiments the SMS cells are generators of flat membranes and appear to be multi-surface feeders. Based on the shape, they appear as surface crawlers and may have extended and oriented sensing.

In some specific embodiments, the SMS cells and cells derived therefrom act as liners (i.e., initiators of extensive linear cell assembly). In these embodiments, the SMS cells are initiators of multicellular extensive linear assembly.

In other embodiments, the SMS cells and cells derived therefrom act as weavers (i.e., pick Longitudinal Flat SMS derived cells (LFS) assembly cells and reposition those diametrically). These cells exhibit various shapes and sizes.

Also provided herein are methods for treating or preventing a disease or condition comprising introducing SMS cells described herein into a subject. In some specific embodiments, the disease or condition is a liver disease, kidney disease, cardiovascular disease, diabetes, cancer, burn, spinal cord injury, retinal disease, arthritis, genetic defect, neurologic disease or immune-mediated disease. In other specific embodiments, the cancer is leukemia or lymphoma; the neurologic disease is a neurodegenerative disease or condition. In various embodiments, the neurodegenerative disease or condition is Parkinson's, Amyotrophic lateral sclerosis or Alzheimer's disease.

Also provided herein are methods for treating or preventing age related conditions comprising introducing SMS cells described herein to a subject. In specific embodiments, the age related condition is cosmetic in nature.

In some embodiments, provided herein are methods for preventing the loss of or generating new functional cells to repair a tissue or organ in a patient by administering SMS cells described herein.

In other embodiments, provided herein are methods for testing the safety and efficacy of a drug in a patient comprising preparing an isolated cell line described herein, exposing the isolated cell line to a drug, and evaluating the safety or efficacy of the drug in the cell line.

Also provided herein are industrial uses of the cell lines described herein. In some specific embodiments, the SMS cells are useful for the production of one or more proteins. In other specific embodiments, the SMS cells are useful for the production of a compound.

Other features and advantages of the present disclosure will become more readily apparent to those of ordinary skill in the art after reviewing the following detailed description and accompanying drawings.

BRIEF DESCRIPTION OF THE DRAWINGS

The details of the present invention may be gleaned in part by the study of the accompanying drawings, in which:

In FIG. 1A, the cytoplasm is hardly visible as a shadow. FIG. 1B illustrates SMS cultured multi-cellular layers appearing opaque. At the bottom of a flask; extracellular matrix made by in vitro cultured SMS cells, stained with safranin are illustrated. In FIG. 1C, the three arrows point to the distinctive three sub-layers.

FIGS. 4D, 4E and 4F illustrate various complex structures derived from the supernatant fraction.

FIG. 16A is digitally enhanced and subjected to inversion (FIG. 16B).

FIG. 42A was subjected to enhancement and digital inversion.

DETAILED DESCRIPTION OF ILLUSTRATIVE EMBODIMENTS

After reading this description it will become apparent to one skilled in the art how to implement the invention in various alternative embodiments and alternative applications. However, although various embodiments of the present invention will be described herein, it is understood that these embodiments are presented by way of example only, and not limitation.

The invention described and elaborated herein refers to by us discovered human Small Mobile stem cell line (SMS) (Rahmo et al (2013) 1 Journal of life sciences and technologies 56-61) its isolation, and its differentiation into other cell types and to multicellular macrostructures. While the present application is exemplified using the SMS stem cell line derived from the human cord blood and from peripheral blood, this is not intended to limit the scope and subject of the present application and those skilled in the art will recognize that the novel stem cell type its isolation, differentiation and resulting complex cellular macrostructures described herein may be derived from a variety of different tissue sources that include SMS cells.

Figure 1A:
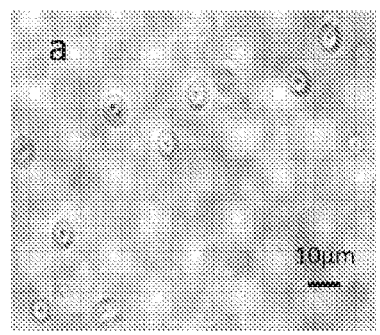
FIGS. 1A-C exemplify images of cultured SMS cells, derived from UCB, with typical circular shape of the nucleus (~3 μm) and the small dark circle in the middle of the nucleus, according to one embodiment of the invention.
Figure 1B:
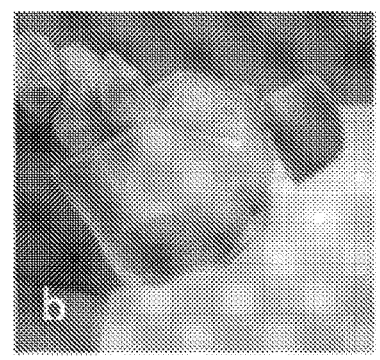
Figure 1C:
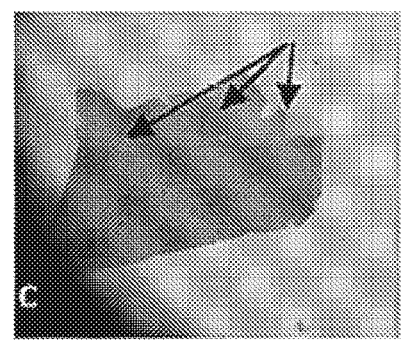
Figure 3A:
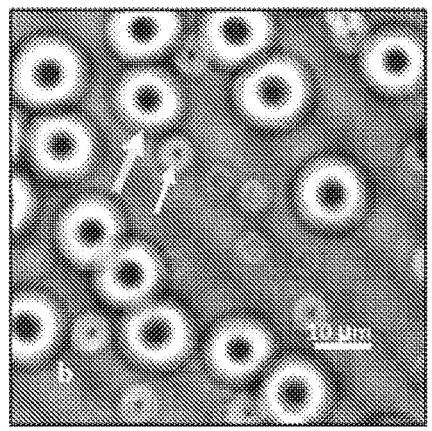
FIGS. 3A-C illustrate that the Coculture of SMS cells (small circular cells) and human red blood cells (large circular cells) both exhibit the surface invagination (arrows) detected as contrast light variations through microscopically varying the focusing plane (FIG. 3A). In vitro cell culturing demonstrating self organization of SMS cells and SMS derived cells resulting in complex assembly of various specific structures. In these embodiments there is a strait cell alignment by anisotropic aggregation (FIG. 3B). Amido black staining of slide preparations showing a complex multilayered structure that includes multi-membranes associated and/or concomitant with SMS and SMS derived cells (FIG. 3C).

The present invention arose from the present inventors initial observations of very small sized adherent cells (~5 µm) in a standard cell culture system. These uniquely shaped SMS cells were equi-dimensional, with strict radial symmetry. They exhibit in a light microscope a translucent cytoplasm, and a circular nucleus (~3 µm) that includes a centrally located very small circle (~1 µm) of different light contrast. Depending on focusing plane, the minute circle appeared darker or lighter. These, throughout cell culture, stable contours of the small cell bear resemblance to the shape of a human "Iris" (see, e.g., FIG. 1A). The observed concentric inner circle appears to be a result of cell surface invagination. This observation is comparable to what is microscopically perceived for the biconcave surface structure of red blood cells (see, e.g., FIG. 3A).

SMS cells were clearly distinguished following 3-4 weeks of cell culture initiation. Cells with the described appearance did not stain with any of the standard Staining techniques (giemsa, methylene blue, Papanicola, and Wright staining) (see, e.g., FIG. 3C). SMS cells strongly adhered to plastic, and detachment using trypsin recipes was unsuccessful. Cells were therefore dislodged using a scraper or through cold shock treatment. Primary culture cells reached confluency in 3-4 weeks. SMS cells were able to proliferate into a multilayer. SMS cells were continuously cultured for over two years (30+ passages), with no apparent effect on proliferation potential.

Exploring further characteristics of SMS cell type demonstrated its responsiveness to common differentiation inductive media, including but not limited to osteogenic, adipogenic and neurogenic media. Cells were cryopreserved at different passages and successfully revived in the same growth medium (Rahmo et al (2013) 1 (1) Journal of life sciences and technologies 56-61).

The present invention was not anticipated based upon the current state of the art. SMS cell type has a unique overall shape (size and the particular form) among reported human stem cells and other reported human cells.

Cell Separation

SMS cells from whole blood were isolated based mainly on strong plastic adherence. Mononuclear cell fraction was recovered by diluting each 10 mL UCB sample with an equal volume of PBS, layering over an equal volume of Ficoll-Paque (1.077 g/ml) (GE health care Biosciences AB, Sweden). Mononuclear cells (MNCs) from the gradient interface were washed twice with PBS after centrifugation at 400 g for 30 min. The layer of sedimented red blood cells was also collected; it represented the RBC fraction. The cell fraction positive for CD34 was isolated from the MNC fraction based on magnetic microbead selection procedure. High-gradient magnetic field and MiniMACS (MS) columns were used (Miltenyi Biotech, Germany).

Cell Isolation and Culture

Whole UCB was used for culture after testing negative for bacterial or fungal contamination. The adherent heterogeneous population of cells was observed on days: 4 and 5. Through continuous change of medium, the suspended cells became gradually fewer. Cells of various shapes appeared at the bottom of culture flasks. The SMS cells were observed as was described in Rahmo A., et al.: Introducing a novel human stem cell with exceptional characteristics: Small, Mobile Stem Cells (SMS). *JOLST* 2013, 1:56-61.

Primary culture cells reached confluence in 3-4 weeks. SMS cells were able to proliferate into a multilayer. SMS cells were continuously cultured, starting 11-2010 till 7-2012 and further (27+ passages), with no apparent effect on proliferation potential. Cell separation using Ficoll density gradient centrifugation, indicated that SMS cells are enriched in the RBC layer. The same cells however have been also isolated from the MNC layer; mainly as a CD34+ fraction.

Testing the presence of SMS cells in blood of animals, including but not limited to rats, using essentially the same methods of isolation resulted in the same outcome observed for human tissue. Further evidence of the presence of SMS cells we obtained from the dissection of various tissues from various organs of Rat and Sheep. See, e.g., FIGS. 17-30 (rat) and FIGS. 31-39 (sheep).

Resistance to Adverse Conditions

SMS cell line demonstrated extraordinary resistance to various non-physiological conditions. These include low and high temperature, freezing and thawing at −20° C. in standard growth medium (Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 µg/mL streptomycin (Gibco)), dehydration, high PH values, and variations in ionic strength.

SMS cell line were grown in absence of any added serum that is in (Low-glucose Dulbecco's Modified Eagle's medium LG DMEM (Gibco) with GlutaMAX™, 100 U/mL penicillin, and 100 µg/mL streptomycin (Gibco)) incubated at 37° C. and 5% $CO_2$ in a humidified atmosphere using the incubator (SHEL LAB, USA) for months with no apparent effect on shape or adverse effects on proliferation potential of SMS cells.

Cell Mobility

The characteristics of cell movements are some of the parameters that define specific cells. Cells vary, for instance, considerably in their speed; fibroblasts move very slowly (12-60 µm/h), while neutrophiles, thought to be the fastest moving human cell, reach speeds of 30 µm/min (Persson et al. (2010) "Cell motility studies using digital holographic microscopy,". in: Microscopy: Science, Technology, Applications and Education. A. Mendez-Vilas, J. Diaz, Ed. FORMATEX 1063, Ch 35.).

Figure 2:
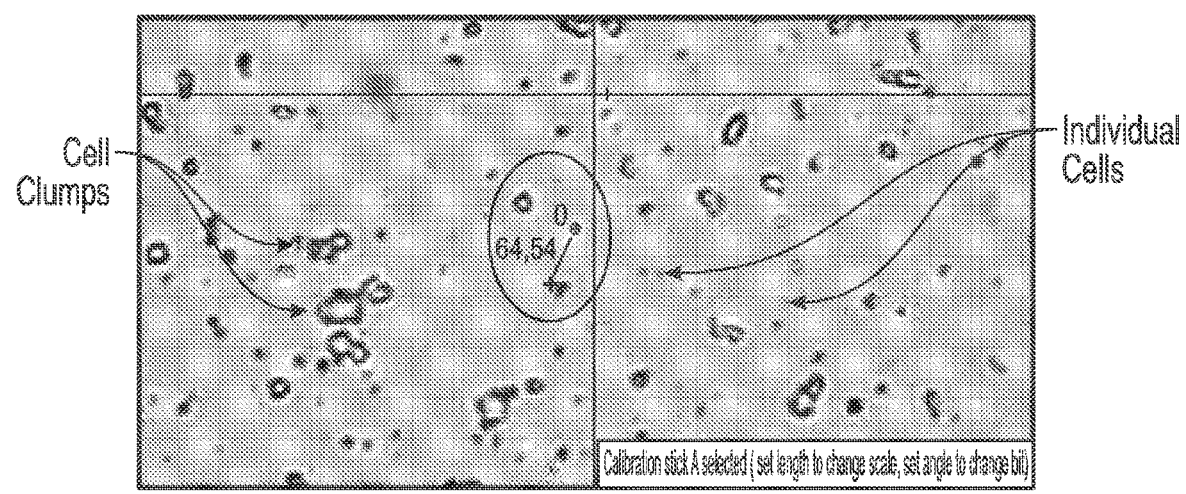
FIG. 2 exemplifies, the path of the moving SMS cell as tracked by the Tracker software and according to one embodiment of the invention. The white arrows in the image point to single cells and cell clusters. Illustrated in the bottom box is a plot diagram of movement time relative to X coordinate position of the cell (circled).
Figure 2:
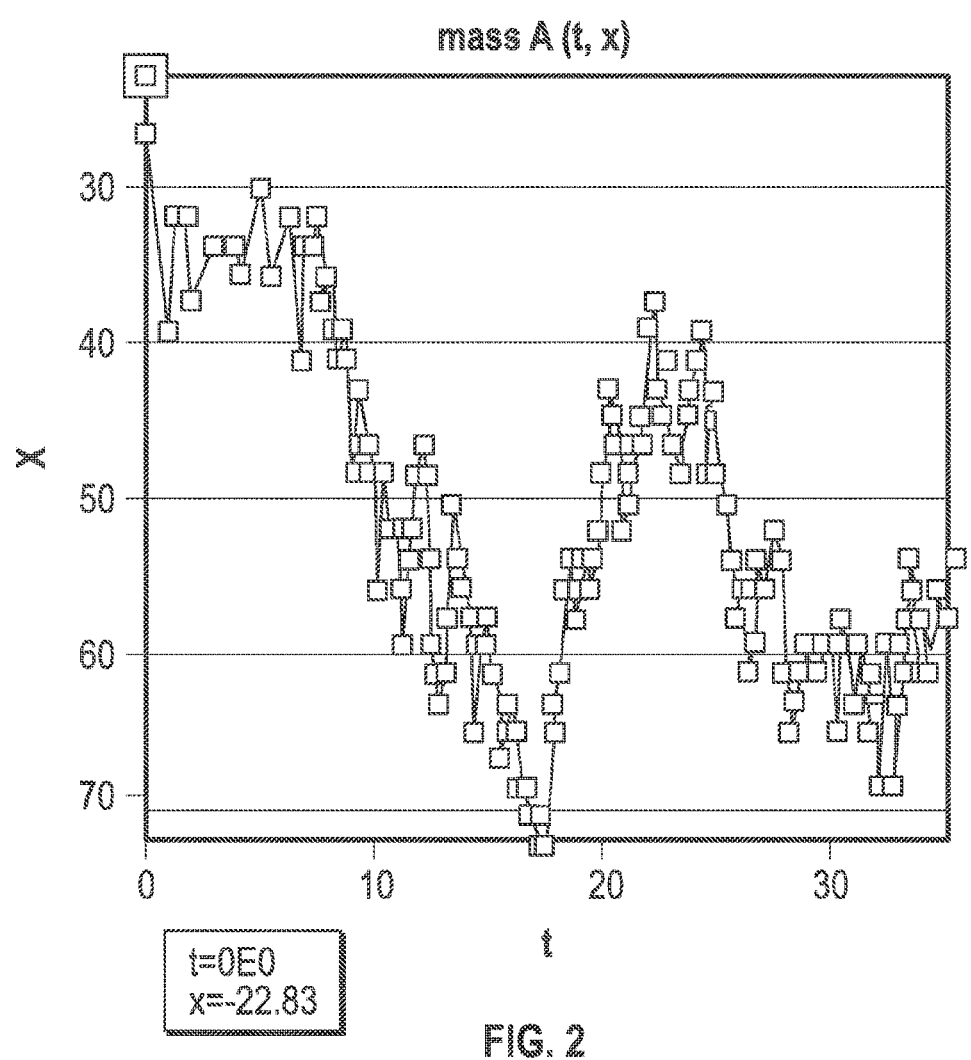

Cell movement is of particular importance to issues of organogenesis, tissue repair and malignant cell invasion. Fast cellular movements were microscopically observed real time in some cells; that is during normal cell culture conditions. Cell speeds of about 1.5 µm/sec were readily measured (see, e.g., FIG. 2). Such fast cellular movements can be induced in almost the entire cell population; that is by applying what can be categorized as adverse cellular conditions (PH shock, cold chock, dislodging). Cellular movement was also observed in cell cultures containing osteogenic inductive media; in this case whole clusters of cells appeared to be dragged by single cells. The motile features of SMS cell line were quite surprising, since obtained speed values exceeded that of neutrophiles; they are therefore an important defining feature of SMS cells.

Cell movements include also movements characterized by a cell cluster moving collectively (i.e., remaining in contact during movement). Collective movement is now widely recognized in embryogenesis and cancer (Mayor et al. (2010) 20 (6) Trends Cell Biol 319-28). SMS fast moving cells allow observation in short time intervals; in which holding culture parameters constant is easily achieved. Accordingly, they serve as an important model, amenable for studying such complex tissue pattern forming movements (Rahmo et al (2013) 1 (1) Journal of life sciences and technologies 56-61).

Multilayer Formation

SMS cell lines display a robust proliferative potential with formation of cellular multilayer in vitro using the growth medium including serum and the one excluding serum and in the absence of any added substance such as matrigel or cell extracellular matrix proteins.

Extensive ECM Production

SMS cell lines are able to co-synthesize organized layers of ECM during extensive cell proliferation. Following few weeks of cell culturing in growth medium, a complex organization of cells and extracellular matrix (ECM) was observed. Some of these structures are organized as layers of membranes that include SMS cells, SMS derived cells, and complex cell assemblies (see, e.g., FIG. 1C, FIG. 3C, FIG. 16A, FIG. 16B).

Three dimensional polymers mimicking ECM, as well as reconstituted basement membrane, such as commercial product Matrigel, have been shown to promote cell organization and differentiation (Gwendolen et al. (2010) 43 (1) Journal of Biomechanics 55-62).

Matrix topography and its physical characteristics are proven to be influential parameters. It is thought that at 3D culture condition cellular gene expression would mirror more closely the in vivo state. Applications included the monitoring of tumor growth and metastasis, tissue engineering, and organ printing.

Macrostructures

Regular multicellular pattern formation was observed during cell culture; especially in the presence of inductive media. Non-limiting examples of inductive media useful in various embodiments of the present invention include: a Neurogenic Differentiation Medium such as: 1 mM b-mercaptoethanol (BME) added to growth medium for 24 h followed by treatment with 2% DMSO and 200 mM butyrate hydroxyanisole (BHA) in growth medium without Fetal bovine serum (see, e.g., X. Q. Kang, W. J. Zang, L. J. Bao, D. L. Li, X. L. Xu, and X. J. Yu, Differentiating characterization of human umbilical cord blood-derived mesenchymal stem cells in vitro, 11 Cell Biology International, vol. 30, pp. 569-575, July 2006); an Adipogenic Differentiation Medium such as: growth medium plus: 1 µmol/Ldexamethasone, 5 µg/mL insulin, 0.5 mM isobutyl-methylxanthine, and 60 µM indomethacin (see, e.g., A. Erices, P. Conget, and J. J. Minguell, Mesenchymal progenitor cells in human umbilical cord blood, British Journal of Haematology vol. 109, no. 1, pp. 235-242, April 2000); and/or an Osteogenic Differentiation Medium such as: growth medium plus: 0.1 µM dexamethasone, 0.05 mM ascorbic acid-2-phosphate and 10 mM β-glycerophosphate (see., e.g., N. Jaiswal, S. E. Haynesworth, A. I. Caplan, and S. P. Bruder, Osteogenic differentiation of purified, culture-expanded human mesenchymal stem cells in vitro, J Cell Biochem. vol. 64, no. 2, pp. 295-312, February 1997).

Such complex patterning at individual and multicellular level suggests multiple or extensive changes at gene expression status; echoing the observed gross changes to individual cell architecture and multicellular organization.

The applied standard inductive media resulted in a multitude of clearly distinctive complex multicellular phenotypes. These observations outline the organo-genetic potency of SMS cells. The development of these structures is a continuous dynamic process that requires weeks and involves typical tissue forming cell activities: cell division (symmetric and asymmetric), cell aggregation, and cell differentiation.

Figure 3B:
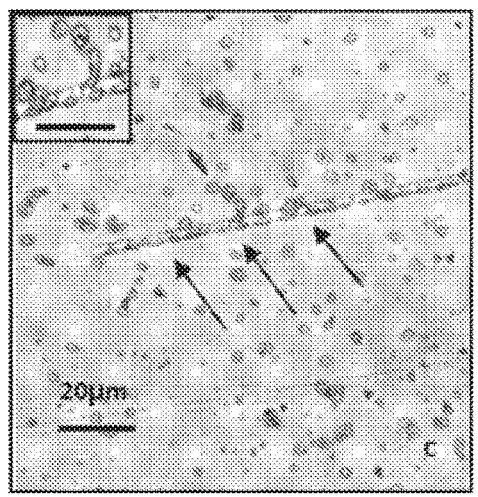
Figure 3C:
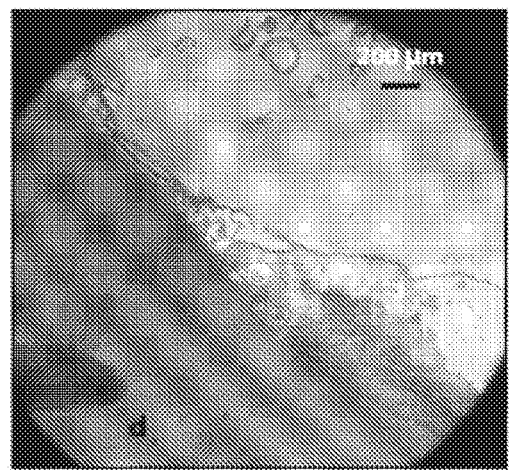

Moreover, cells appear to migrate in a coordinated fashion, to cooperate, and to associate spontaneously, forming complex cell-ECM structures of various compositions; some of which are transient (see, e.g., FIG. 3B).

Fractions of tissue like structures and its components may detach spontaneously from the adherent fraction of the flask and were examined in the supernatant suspension of the cell culture. The main fraction remained adherent to the flask, and was detached by scraping for subculturing or examination (Rahmo et al. (2013) 1 (1) Journal of life sciences and technologies 56-61).

Cryopreservation

A Trypan-blue dye exclusion test was used to distinguish the cell viability (Invitrogen). Cell number and viability were estimated using the Countess® cell counter (Invitrogen). Cells were cryopreserved using a freezing medium consisting of 60% growth medium with 30% FBS and 10% DMSO.

The present invention teaches the presence of a new cell type with exceptional characteristics. This cell type is very small in size, has a regular characteristic nuclear shape and a very translucent cytoplasm. SMS cell lines are very fast in terms of mobility, but attach very strongly to plastic and very poorly to normal glass. They do not stain with many standard staining techniques. SMS cell lines proliferate in standard media for more than 30 passages, are quite resistant to adverse conditions, form a multilayer, excrete ECM, can be grown in absence of serum and have a capability of forming complex multicellular macrostructures. The exceptional characteristics of this cell type assert clearly its novelty among earlier described stem cells.

Indeed, this novel cell line provide significant advances of the prior state of the art. Although many different stem cell lines and processes for their isolation and utilization exist and are being examined, the procedures related to them have shortcomings. For example, none of them provide the following SMS cell line advantages: (1) the ability to isolate SMS cells from various organs including cord blood and peripheral blood; (2) the ability to proliferate for extensive long period of time in modest media; (3) the ability to proliferate in media supplemented with human serum or without any added serum (basic medium without additives); (4) resistance to adverse conditions (such as low and high temperature, pH changes, dehydration); (5) the ability to provide for autologous transfer of these stem cells, and cells derived from it, in high quantity; (6) the ability to differentiate into multi-cellular complex structures; (7) the ability to provide for autologous transfer of differentiated tissue, identical or tissue like structures produced in vitro; and (8) the ability to synthesize and produce extracellular components of potential therapeutic and industrial uses.

EXAMPLES

Example 1: Cell Culture and Cryopreservation

Cells from whole peripheral blood, whole umbilical cord blood mononuclear fraction and RBC fraction were cultured separately and allowed to adhere to the bottom of the T25 flask (Techno Plastic products TPP).

Culture was initially incubated in growth medium for four days. Medium changes were carried out twice weekly thereafter. Growth medium used was Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 μg/mL streptomycin (Gibco) incubated at 37° C. and 5% $CO_2$ in a humidified atmosphere using the incubator (SHEL LAB, USA).

At later stages only half the medium was weekly changed. Cells were usually passaged upon reaching 80% to 90% confluency using a scraper or cold shock treatment (~1 h at 4-8° C.). Primary culture cells reached confluency in 3-4 weeks. SMS cells were able to proliferate into a multilayer (at least three layers) (see, e.g., FIG. 1C).

Lower layer cells became attached more strongly to the surface of the flask through a layer of extra cellular matrix (ECM). Cells were cryopreseved at different passages in cryopreserving medium (60% growth medium, 30% added FBS, 10% DMSO) and successfully revived in the same growth medium.

Example 2: Osteogenic Differentiation

Following treatment with inductive medium, cells grown from umbilical cord blood, were subcultured in growth medium (Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 μg/mL streptomycin (Gibco) incubated at 37° C. and 5% $CO_2$ in a humidified atmosphere using the incubator (SHEL LAB, USA)) for 24 hours and then subjected to osteogenic medium (growth medium plus: 0.1 μmol/L dexamethasone (Sigma), 0.05 mmol/L ascorbic acid-2-phosphate (Sigma) and 10 mmol/L β-glycerophosphate (Sigma)) (Jaiswal et al. (1997). 64 (2) J Cell Biochem 295-312).

Medium changes were performed every 3 to 4 days. The media, containing detached cells and tissues of each flask, were centrifuged. Collected pellets were separately cultured at the same conditions, using a tissue culture flat tube (TPP); representing the supernatant fraction. A fraction of cells changed drastically their shape and size; becoming larger and exhibiting standard cell morphology, with clear nuclei and cytoplasma.

Figure 4A:
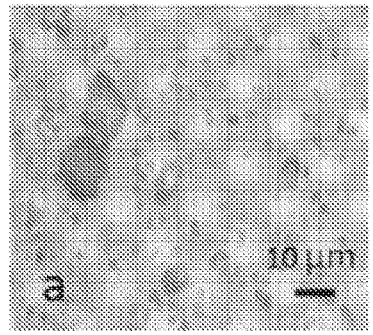
FIGS. 4A-F exemplify SMS cells derived from UCB cultured m osteogenic differentiation medium, according to some embodiments of the disclosure. Assembly into complex structures; the adherent fraction (FIG. 4A); the supernatant fraction (FIG. 4B). Structures, stained with alizarin Red S (FIG. 4C).

A percentage of cells (~30%) aggregated and tended to lessen attachment to surface. Some aggregated cells formed assemblies of different shapes, with or without color (see, e.g., FIG. 4A). A fraction of aggregated cells gained a clear orange color and formed a complex assembly that became brownish (see, e.g., FIG. 4A).

Figure 4B:
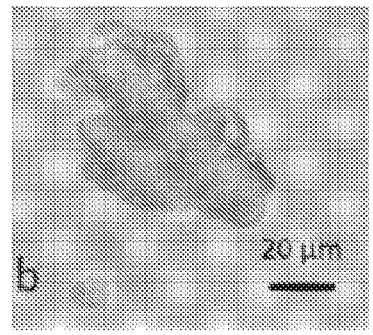

Many of these, and some rather complex structures, were present in the supernatant fraction (see, e.g., FIG. 4B). This differentiation medium induced apparently the formation of several different cell assemblies (see, e.g., FIG. 4D, FIG. 4E, FIG. 4F). Many cells were stained strongly with the dye Alizarin Red S.

Figure 4C:
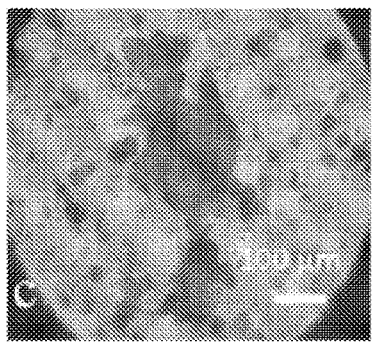
Figure 4D:
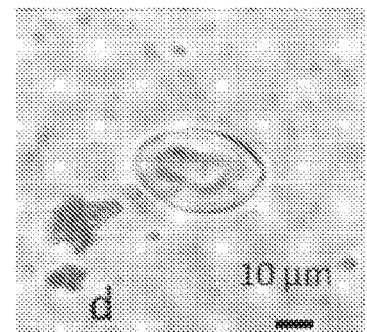
Figure 4E:
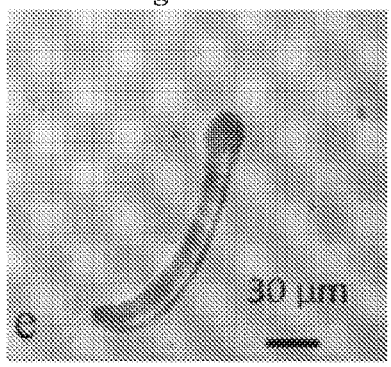
Figure 4F:
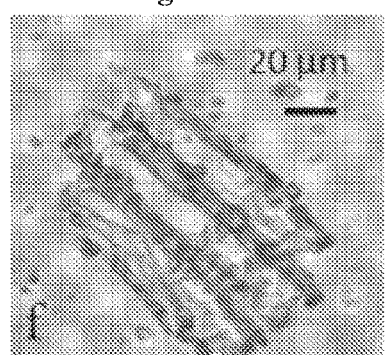

Some of the complex assemblies of cells were also stained; indicating accumulated calcium deposits (see, e.g., FIG. 4C). The staining pattern was comparable to the one observed in a sheep bone control sample. Throughout culture, a large fraction of cells maintained the pre inductive shape of SMS cells and continued to proliferate. Following six weeks of incubation with inductive medium, cells were reincubated with the original growth medium. This caused disassembly of aggregated cells, and disappearance of some earlier formed complex structures (within ~2 weeks).

Example 3: Adipogenic Differentiation

Inductive medium, cells grown from umbilical cord blood, were subcultured in growth medium at standard conditions (Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 μg/mL streptomycin (Gibco) incubated at 37° C. and 5% $CO_2$ in a humidified atmosphere using the incubator (SHEL LAB, USA)) for 24 hours, and then grown in adipogenesis medium (growth medium plus: 1 μmol/L dexamethasone, 5 μg/mL insulin, 0.5 mmol/L isobutylmethylxanthine, and 60 μmol/L indomethacin) (Erices et al (2000) 109 (1) British Journal of Haematology 235-242).

Figure 5A:
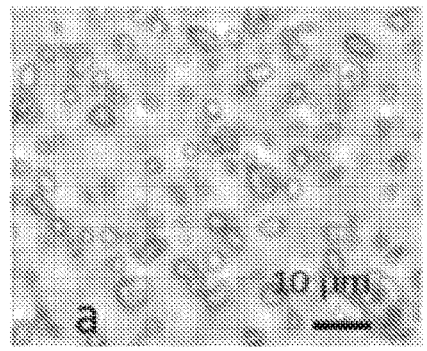
FIGS. 5A-C exemplify SMS cells derived from UCB; cultured in adipogenic differentiation medium according to some embodiments. The shape of cells indicates drastic morphological changes (FIG. 5A), assembly of cells into complex structures (FIG. 5B). Complex tissue-like structures stained with Oil Red 0 are illustrated in FIG. 5C.

Half the medium was changed twice weekly. The media of each flask were centrifuged. Collected pellets were separately cultured at the same conditions using a tissue culture flat tube (TPP); representing the supernatant fraction. Inductive medium caused many SMS cells to become larger; starting day 2, and some aggregated (see, e.g., FIG. 5A).

Figure 5B:
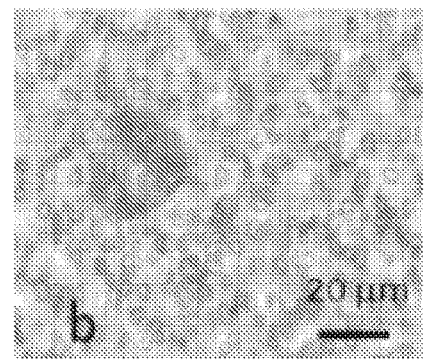
Figure 5C:
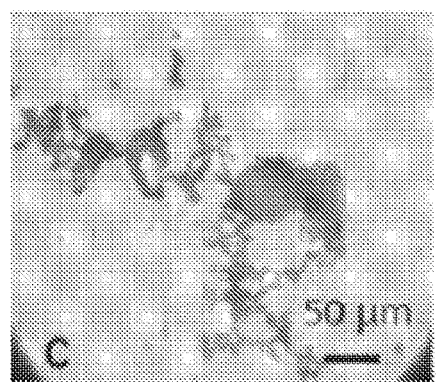

Some cells appeared to accumulate lipid droplets of yellow color. Oil Red 0 staining, demonstrated a rich lipid deposit in some cells. Aggregated cells formed multicellular assemblies with fat deposits (see, e.g., FIG. 5B). Many of these were present in the supernatant fraction (see, e.g., FIG. 5C). After 10 days, flask inductive medium was replaced with the original growth medium causing the former phenotype to disappear (2 weeks). Cells appeared to have reversed back to the original pre-inductive morphology.

Example 4: Neurogenic Differentiation

Cells grown from (peripheral and umbilical cord blood) were seeded separately in T25 flasks (TPP). At 70% confluency, 1 mM beta-mercaptoethanol (BME) was added to growth medium at standards conditions (Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 μg/mL streptomycin (Gibco) incubated at 37° C. and 5% $CO_2$ in a humidified atmosphere using the incubator (SHEL LAB, USA)) for 24 h. Cells were washed with D-Hanks buffer solution three times, and treated with 2% DMSO and 200 mM butylatedhydroxyanisole (BHA) in the same growth medium but without FBS (Kang et al (2006) 30 Cell Biology International 569-575).

Cell morphology was observed using an eclipse TS100 (NIKON) inverted microscope and photographed with a cybershot (Sony) camera, in room temperature. Cells were cultured further in the same flask for several weeks, using the same inductive medium. Half the medium was replaced twice weekly.

Figure 6A:
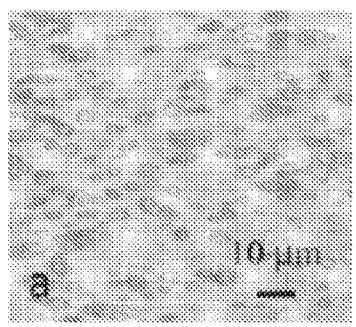
FIGS. 6A-F illustrate SMS cells derived from UCB in cultured neurogenic differentiation medium (FIG. 6A, FIG. 6B) and cell assembly following early induction (FIG. 6C). The shape of various silver stained cells appearing black or dark brown is consistent with neuronal silver staining (FIG. 6D, FIG. 6E). Assembly of differentiated cells after several weeks of induction is illustrated in FIG. 6F.

Following treatment with β-mercapto ethanol no visible changes were observed. After treatment with the second inductive medium, responsive cells (~60%) changed shape, became in some cases extended, and a fraction of these cells became later thicker and refractile (see, e.g., FIG. 6A). Some cells became larger, but maintained an approximate spherical shape. Both cells formed branches. Some appeared multi polar, (see, e.g., FIG. 6A).

Figure 6B:
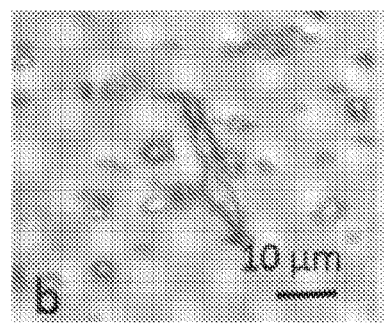
Figure 6C:
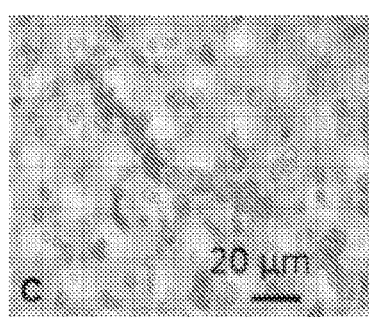

Some cells have their branches reaching to other cells and appeared to create intercellular contact (see, e.g., FIG. 6B). Some of the drastic changes observed were within hours; while most appeared the next day. Cells remained adherent to flask. Further incubation with inductive medium at 37° C. and 5% $CO_2$ for 30 days induced more significant changes to cell shape and organization. Continuous cell growth and the formation of multi-layers were observed, despite the absence of FBS in the neuronal inductive medium.

Figure 6D:
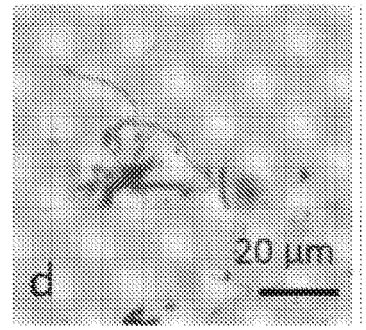
Figure 6E:
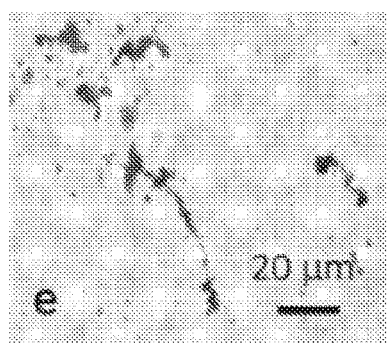
Figure 6F:
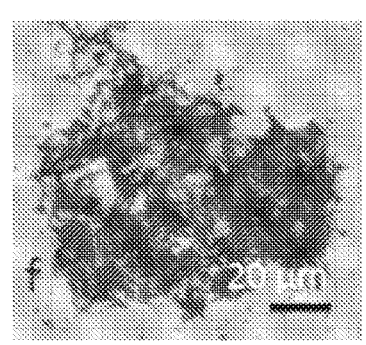

Detaching induced cells and centrifugation resulted in a larger, clearly gray colored pellet, which was in contrast to the usual small white pellet of SMS cells; in absence of inductive media. Staining these cells indicated the presence of various argyrophilic cells, with a shape characteristic to neuronal cells (see, e.g., FIG. 6D, FIG. 6E, FIG. 6F).

Some cells maintained SMS pre-inductive shape and continued to proliferate in the presence of inductive medium. At the bottom of the multilayer grown cells, a complex, dense, mainly cell free layer appeared which constituted the ECM attached to the base of the flask. Reversing post inductive cell shape by re-incubating in growth medium was not observed in this case Example 5: Macrostructuring Following few weeks of cell culturing in standard growth medium and standard conditions (Low-glucose Dulbecco's Modified Eagle's medium LG DMEM (Gibco) with GlutaMAX™ and supplemented with 10% heat inactivated fetal bovine serum (FBS) (Invitrogen), 100 U/mL penicillin, and 100 μg/mL streptomycin (Gibco) incubated at 37° C. and 5% $CO_2$ in a humidified atmosphere using the incubator (SHEL LAB, USA)) a complex organization of cells and extracellular matrix (ECM) was observed. Some of these structures are organized as layers of membranes that include SMS cells, SMS derived cells, and complex cell assemblies (see, e.g., FIG. 3C).

Fractions of this tissue like structure and its components detach spontaneously from the flask and were examined in the supernatant suspension. The main fraction remained however adherent to the flask, and were detached by scraping for subculturing or examination.

The development of these structures is a continuous dynamic process that requires weeks and involves typical tissue forming cell activities: cell division (symmetric and asymmetric), cell aggregation, and cell differentiation. Moreover, cells appear to migrate in a coordinated fashion, to cooperate, and to associate spontaneously, forming complex cell-ECM structures of various compositions; some of which are transient (see, e.g., FIG. 3B).

Despite the complexity and diversity of the observed cell-ECM structures, the process leading to these structures is highly reproducible. Partial or even extensive scrapping of the flask, leads to regeneration of the same structures. Repeated scrapping of emerging cultured Cell-ECM complex assemblies and its analysis using various staining techniques, revealed copious details of these diverse highly complex and self-organized structures.

Samples were fixed with 4% paraformaldehyde in PBS for 60 min at room temperature, and wetted with distilled water before staining. Staining solutions were prepared as follows: Staining using Amido black 10B (Merck, CI: 20470): A 1% dye solution was prepared using 7% acetic acid distilled water solution. Staining using Toluidine blue (Reactifs RAL, CI: 52040): 0.1% in distilled water. Staining was for both for 10 minutes followed by rinsing using either a 7% acetic acid distilled water solution for amido black, or distilled water for Toluidine blue staining. Masson Goldner trichrome staining solutions were purchased from Carl Roth GmbH+KG co. and staining was according to instructions.

Highly reproducible structures pertaining (but not exclusively) to tubulogenesis were discerned during various SMS cell derived processes. Pertinent processes are designated as: 1—parallel duplicate membrane incisions, 2—three dimensional cluster mesh assembly, 3—coated tubular assembly, 4—two dimensional leaf mesh assembly and derivatives.

Figure 7:
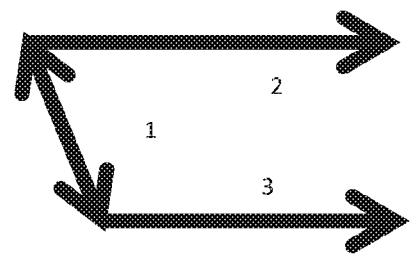
FIG. 7 exemplifies parallel duplicate membrane incisions is initiated by a diametrical incision that may vary in length (1) causing the membrane to expand diametrically; and variation in length through parallel concomitant incision (2, 3), according to some embodiments of the disclosure.

Parallel duplicate membrane incisions: SMS derived cells initially cut the connective membrane to variable distances and then cut at the two ends at fixed angles to the prior incision for extended lengths. Each of these duplicate membrane incisions continue to proceed parallel in an equidistant mode (see, e.g., FIG. 7), resulting in a long stretch of rectangular membrane with constant diameter (see, e.g., FIG. 8A and FIG. 8B). Noticeable is that several of these duplicate incisions that proceeded at various distances, are actually extending parallel to each other (see, e.g., FIG. 8A). This suggests a potential common directive.

Figure 8A:
FIGS. 8A-F exemplify Parallel duplicate membrane incisions: SMS derived cells cut the connective membrane to variable distances and proceed in duplicate parallel membrane incisions continue to proceed parallel in an equidistant mode (arrow) (FIG. 8A, FIG. 8B), resulting in a long stretch of rectangular membrane with constant diameter. In this embodiment, several of the duplicate incisions proceeding at various distances, are actually extending parallel to each other (arrows) (FIG. 8A). Different folding pattern and mostly spiral folding is observed for the partially cut membrane (arrow heads) (FIGS. 8A, 8B, 8C, and 8E). Cells coating the liberated membrane (arrows) convert this structure into what appears to be a tubular structure (FIG. 8D, FIG. 8E). In some cases the membrane is even embedded within membrane during this process (arrow) (FIG. 8F). All images were taken from living cultured cells.
Figure 8B:
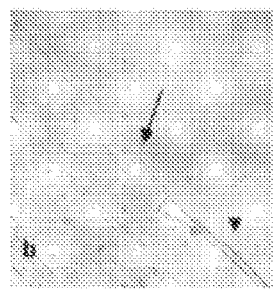
Figure 8C:
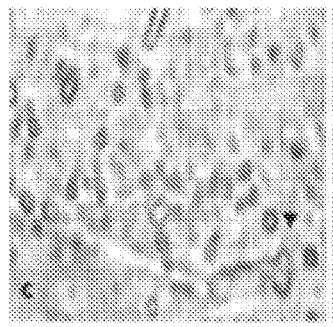
Figure 8D:
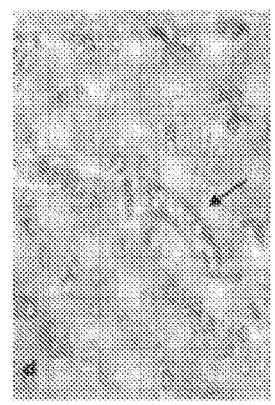
Figure 8E:
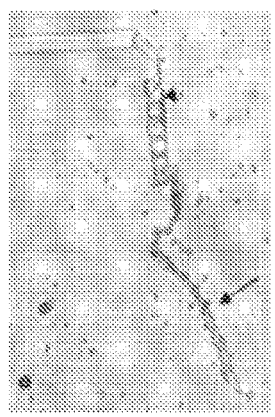
Figure 8F:

Different folding pattern and mostly spiral folding was observed for the partially cut membrane (see, e.g., FIG. 8A and FIG. 8E). This suggests internal physical forces on the membrane. However cells coating the liberated membrane convert this structure into what appears to be a tubular structure (see, e.g., FIG. 8D and FIG. 8E). In some cases the membrane is even embedded within membrane during this process (see, e.g., FIG. 8F). The size of the tube may vary based on the described process. Diametrical incision length, and the distance of the parallel incisions, varies tube's diameter and length.

Figure 9A:
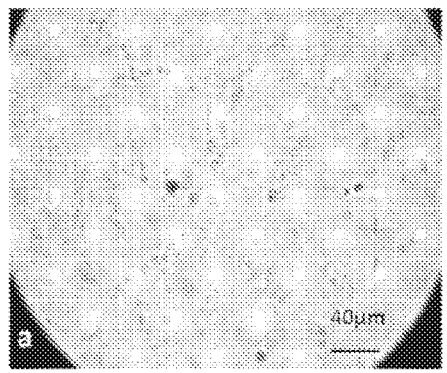
FIGS. 9A-I exemplify three dimensional cluster mesh assembly: Amido black stained slide preparations showing aggregation of SMS cells that form a core with disorderly branches (FIG. 9A, FIG. 9B, FIG. 9C). The circular discoid shaped cells appear to aggregate side by side (FIG. 9C). SMS cells reshape converging their circular invaginations (see arrows at FIG. 9C) forming a continuous groove in associated cells (FIG. 9D, FIG. 9E). Folding (wrapping) of associated cells forms fine tubes of ~3-4 μm diameter. Branches connect and fuse (anastomose) forming a mesh (FIG. 9F, FIG. 9G). For comparison, images of aggregated living cells in a cell culture flask are provided (FIG. 9H, FIG. 9I).
Figure 9B:
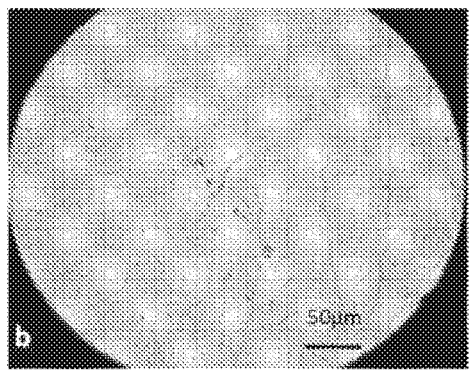
Figure 9C:
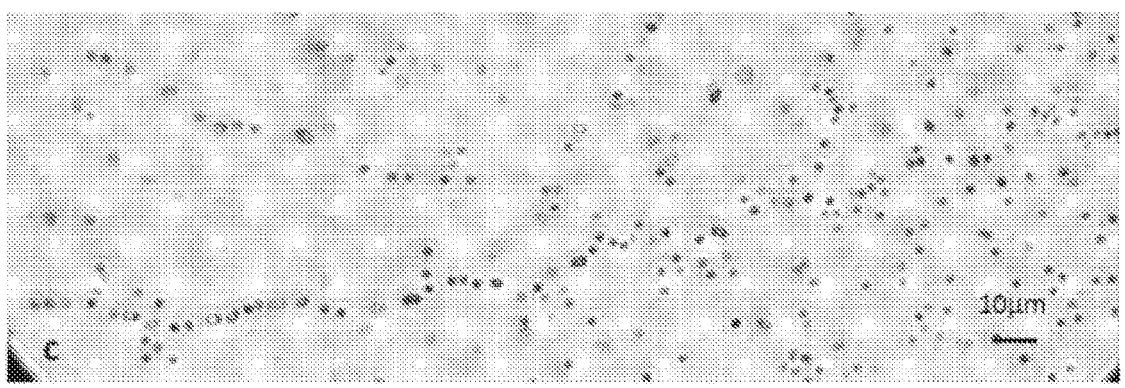

Three dimensional cluster mesh assembly: SMS Cells enlarge slightly, most notably the small inner circle, and aggregate in an organized cluster assembly that lay in 3D embedded within the ECM (see, e.g., FIG. 9A and FIG. 9B). The core of each cluster is approximately linear, composed of single cells. From that main aggregate core, branches extend at irregular intervals and no secondary branches appeared (see, e.g., FIG. 9C).

Figure 9D:
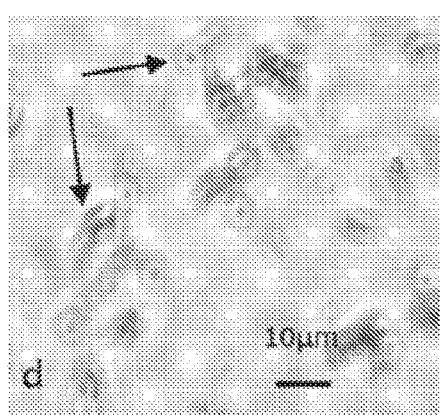
Figure 9E:
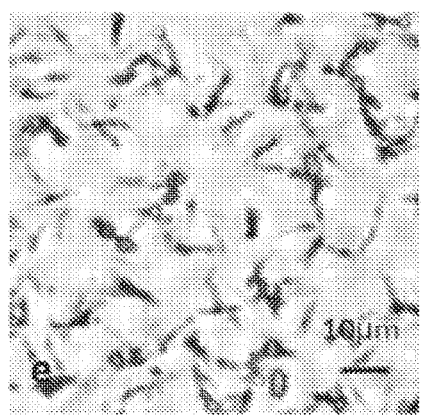
Figure 9F:
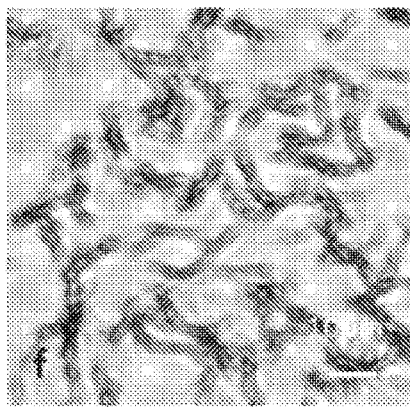
Figure 9G:
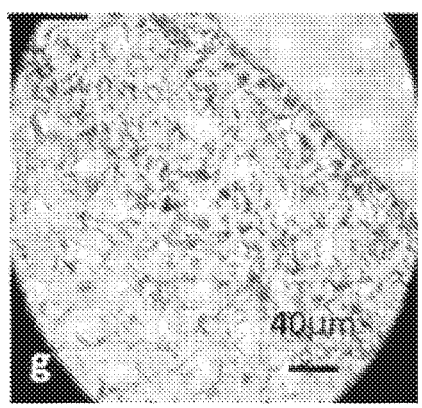
Figure 9H:
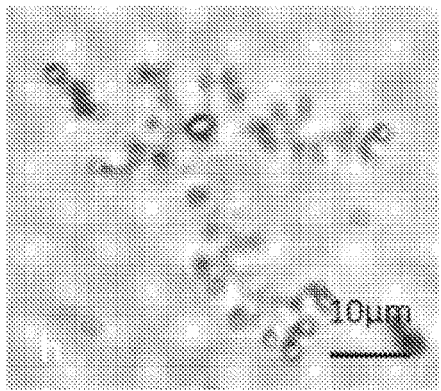
Figure 9I:
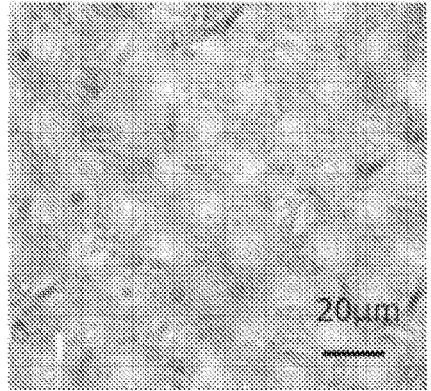

Cells associate topically side by side in a thread like manner (see, e.g., FIG. 9D). Cell's individual surface invaginations converge to form a continuous valley. Folding of outer edges (wrapping) would convert the thread into a potential tube (see, e.g., FIG. 9E, FIG. 9F). Thread assemblies connect (anastomose) creating a dense mesh of a regular diameter as determined by SMS cell dimensions (see, e.g., FIG. 9F). The SMS cells do not undergo major shape changes within this process. Various stages of this process were observed on cultured living cells (see, e.g., FIG. 9H and FIG. 9I).

Figure 10A:
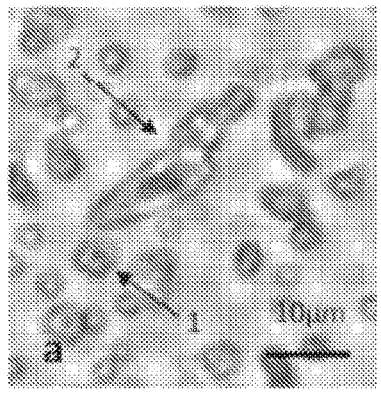
FIGS. 10A-I illustrate a coated tubular assembly according to some embodiments: SMS cells reshape enlarging and forming round cells of darker tone (arrow 1), these cells flatten and extend to become longitudinal (EFS cells) (FIG. 10A); two EFS cells associate (arrow 2) (a); partial and complete wrapping of EFS cells (FIG. 10B, FIG. 10D); extension in length by cellular associations (arrow) (FIG. 10C); coating EFS cells by SMS derived cells (FIG. 10E, FIG. 10F); mobilization of EFS cells into a growing coated tube (FIG. 10G); the growing tube shows branching (FIG. 10H). In some embodiments, large extended tubes separate from the adherent fraction of the flask and appear attached to each other through membrane (FIG. 10I). All images were taken from live cells in culture.
Figure 10B:
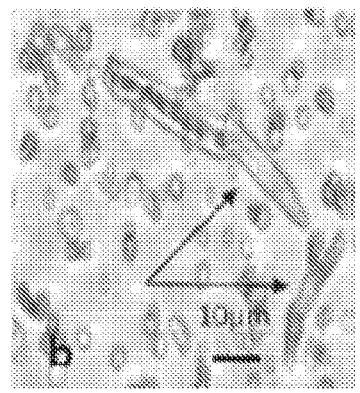
Figure 10C:
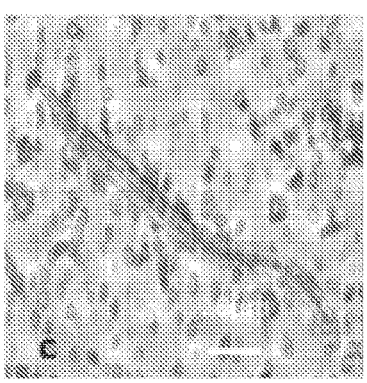

Coated tubular assembly: SMS cells of radial symmetry grossly modify their shape, becoming larger and brownish dark. Such cells were enriched in the CD34 positive fraction isolated by magnetic beads. The cell flattens and converts, by apparently combining with other cells or dividing, into a flat longitudinal SMS (FLS) derived cell assembly. Radial symmetry is converted hence into bilateral symmetry (see, e.g., FIG. 10A, FIG. 10B and FIG. 10C).

Figure 10D:
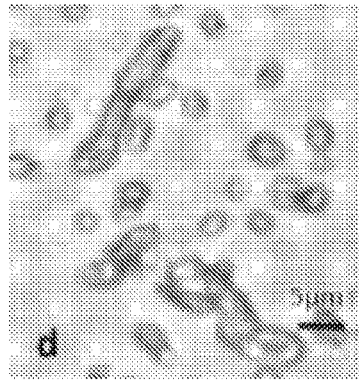
Figure 10E:
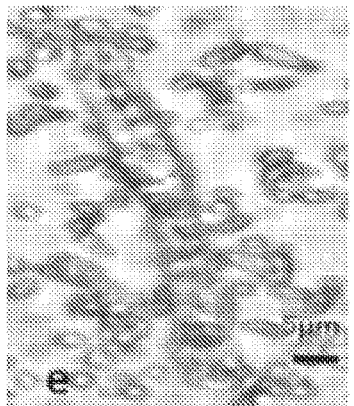
Figure 10F:
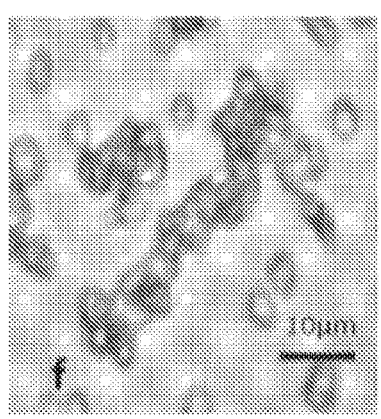
Figure 10G:
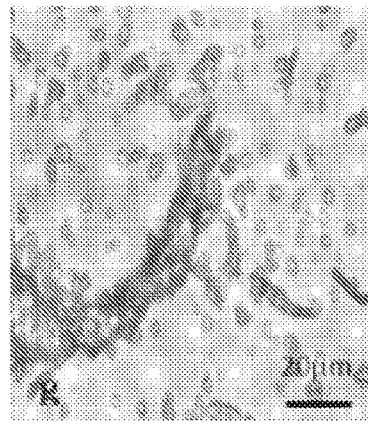
Figure 10H:
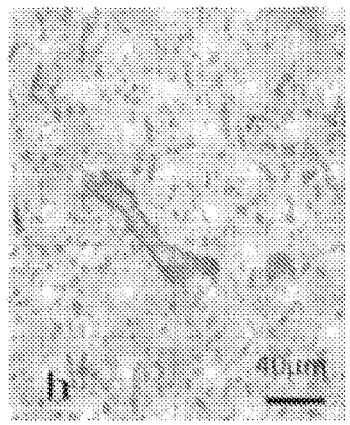
Figure 10I:
Figure 11:
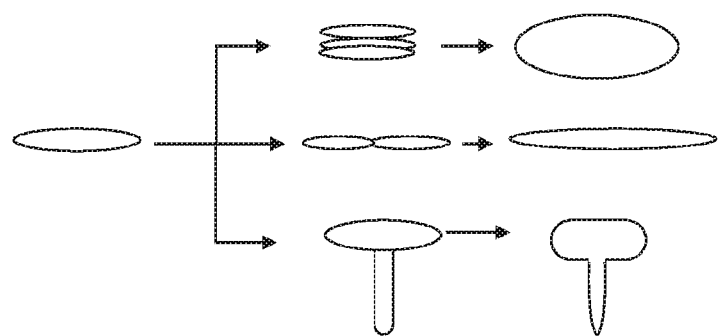
FIG. 11 exemplifies EFS cell assembly able to undergo fusion that may occur: juxtaposed side by side (1) resulting in a diametrically larger tube; tip to tip (2) resulting in an elongated tube; tip to side (3) resulting in branching, according to some embodiments of the disclosure.
Figure 12:
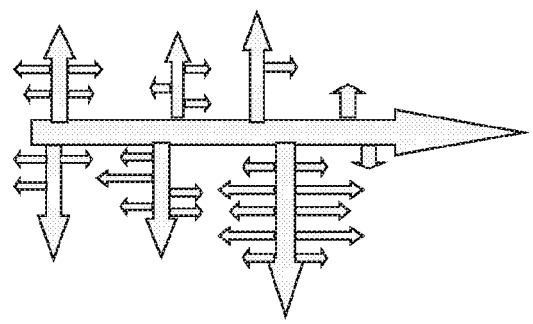
FIG. 12 exemplifies the two dimensional leaf mesh assembly involves extension of a thick core structure and perpendicular primary and secondary branching, according to some embodiments of the disclosure.

Flat Longitudinal SMS derived cell assemblies (FLS) appear to apply a wrapping mechanism for creating a tubular structure (see, e.g., FIG. 10D). Edges of FLS cell assembly fold and connect forming a hollow core (see, e.g., FIG. 10D). SMS derived cells of differing shape are attracted to the assembly, and coat the extended tubular structure (see, e.g., FIG. 10E and FIG. 10F). The coated tubular assembly structure appears to extend by mobilizing other FLS derived cells (see, e.g., FIG. 10G). Depending on FLS association pattern (sideway or at the tip), tubes may grow in length or diameter, or even extend branches (see, e.g., FIG. 10H and FIG. 11). These large structures detach readily from the adherent fraction and are observed floating in media. Occasionally several of coated tubular assemblies are floating, attached by connective membrane (see, e.g., FIG. 10I). This process can be easily observed on living cells in culture.

Figure 13A:
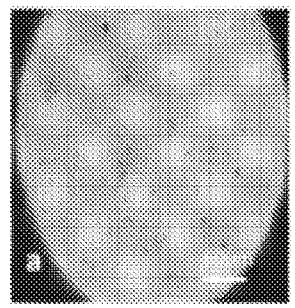
FIGS. 13A-I exemplify a two dimensional leaf mesh assembly according to some embodiments: amido black staining of SMS cell aggregate forming a core with perpendicular branches (FIG. 13A, FIG. 13C, FIG. 13D); primary branches form thinner perpendicular secondary branches (FIG. 13E); the assembly mature (anastomose) into an interconnected mesh; visualized in slide preparations using both amido black staining (FIG. 13F) and toluidine blue (FIG. 13G); Masson Goldner trichrome staining of resulting leaf mesh assembly (FIG. 13H, FIG. 13I). In some embodiments, the same structure is partially visualized using Masson Goldner trichrome staining in culture flask, indicating the presence of hidden leaf mesh assembly (FIG. 13B).
Figure 13B:
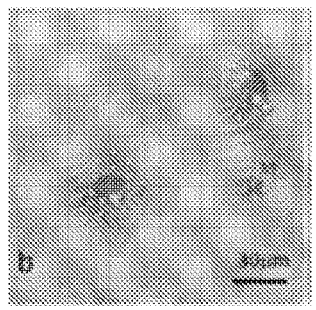
Figure 13C:
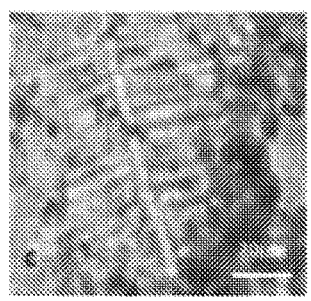
Figure 13D:
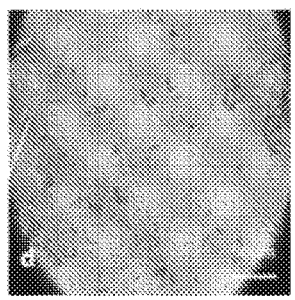
Figure 13E:
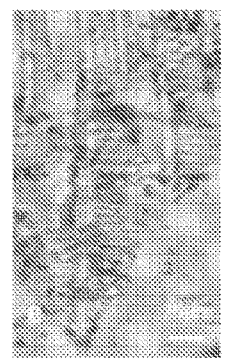
Figure 13F:
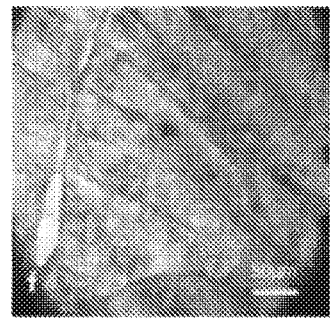
Figure 13G:
Figure 13H:
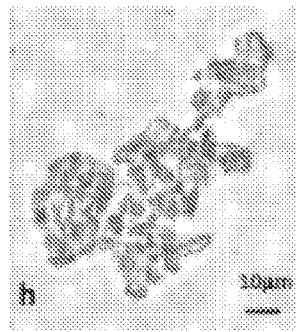
Figure 13I:
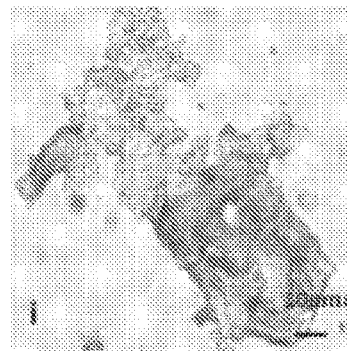
Figure 14A:
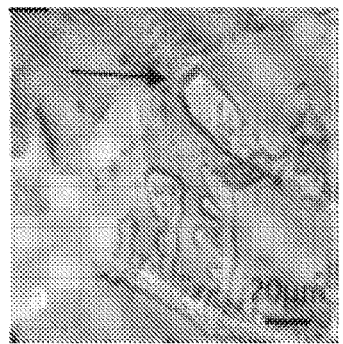
FIGS. 14A-L exemplify crescent formation, membrane tube transition and fenestrations according to some embodiments: Crescent formations appear at the edges of the leaf mesh assembly (arrow) (FIG. 14A); these contain EFS cells that migrate away from the assembly while digesting a membrane layer (FIG. 14B, FIG. 14C, and FIG. 14D); crescent formations migrate into assemblies and fusing into larger crescents as shown by amido black staining (FIG. 14E, FIG. 14F) and toluidine blue staining (FIG. 14G, FIG. 14H). In some embodiments, these represent pretubular membrane folding which are cut out (FIGS. 14I, 14J, 14K, 14L). Some crescent formations combine to form fenestrations within the membrane (window like structures) the diameters of which varies (FIG. 14I, FIG. 14J).
Figure 14B:
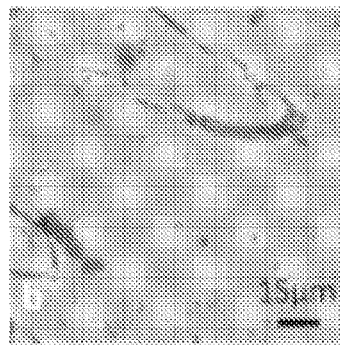
Figure 14C:
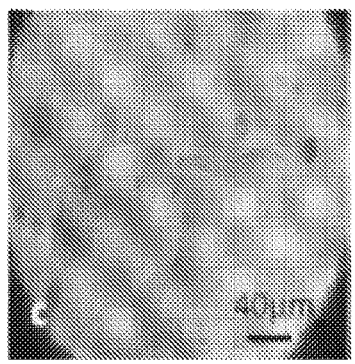
Figure 14D:
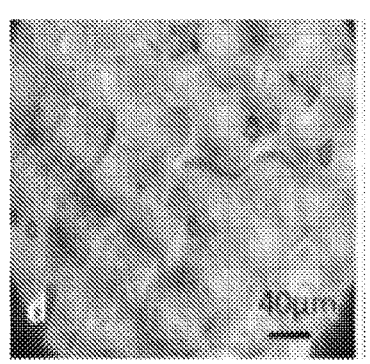
Figure 14E:
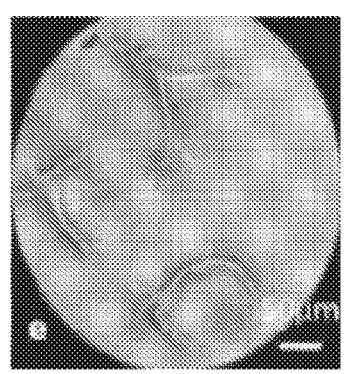
Figure 14F:
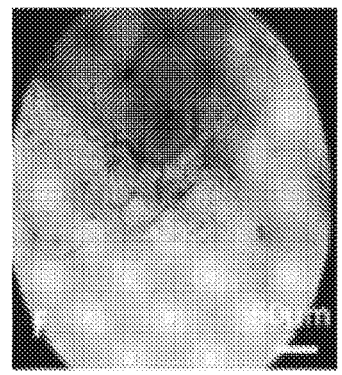
Figure 14G:
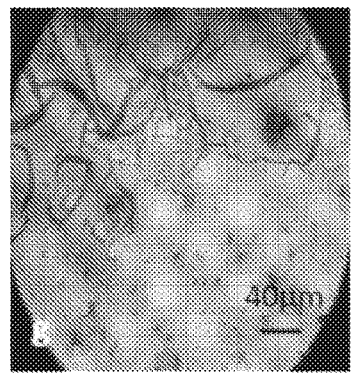
Figure 14H:
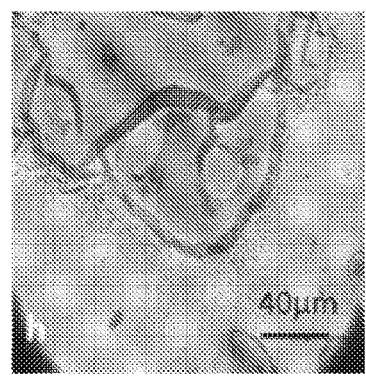
Figure 14I:
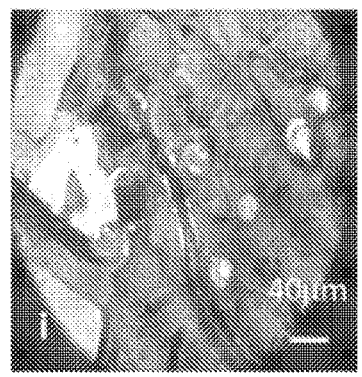
Figure 14J:
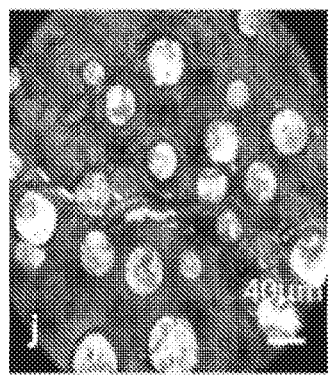
Figure 14K:
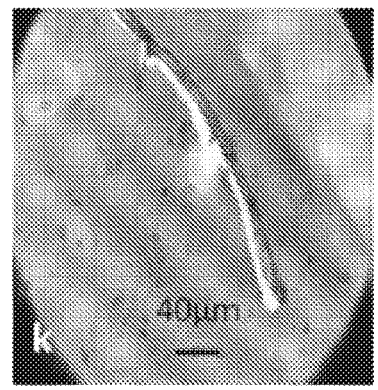
Figure 14L:
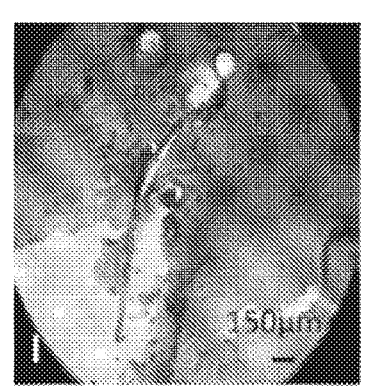

Two dimensional leaf mesh assembly and derivatives (membrane—tube transition by crescent formation, fusion, and slicing, two dimensional membrane fenestration): SMS cells aggregate in a characteristic organized ramification, embedded as a 2D planar complex within ECM. The core is mostly linear. From that core perpendicular branches at regular intervals are extending and yet smaller ones grow at regular intervals perpendicular to primary branches (see, e.g., FIG. 12, FIG. 13A, FIG. 13C, FIG. 13D, FIG. 13E). This leaf vein like formation is quite invisible in unstained culture flask. Merely the portions of the fixed culture flask stained with Masson Goldner trichrome method, reveal the actual presence of the leaf vein like organized assemblies (see, e.g., FIG. 13B). The organized ramification matures into a fine mesh that covers a large surface area and appears rather like a network of fine connecting tubular web (see, e.g., FIG. 13F, FIG. 13G).

Membrane—tube transition by crescent formation, fusion and slicing: Side branches tend to form characteristic crescent structures. They include flat longitudinal SMS cell derived assemblies (FLS) that appear to move in targeted directions. Concomitantly, a membrane layer is being digested in the direction of FLS movement (see, e.g., FIG. 14A, FIG. 14B, FIG. 14C, FIG. 14D). The merger of the crescent structures establishes large membrane folds, representing pre-tubular structures embedded in a planar connective membrane (see, e.g., FIG. 14E, FIG. 14F, FIG. 14G, FIG. 14H). Large pre-tubular structures are further processed by slicing it out from the embedding connective membrane (see, e.g., FIG. 14I, FIG. 14J, FIG. 14K, FIG. 14L). The result is a rather long free nascent tube.

Chronically coordinated asymmetrical cuts, appear to be involved, and may ensure correct membrane curvature, coaxing membrane into predestined tube. The internal stress exerted by the fibrous components of the connective membrane could be an essential contributor to membrane curvature and tube formation. The size of the nascent tube varies depending on the number of crescent fusions at earlier stage. However, even the pre-tube appears to exert the ability to fuse with other tubes (see, e.g., FIG. 14H). Depending on fusion site, the outcome may be a tube of larger diameter, or extended length, or the formation of a branching tube (see, e.g., FIG. 11 and FIG. 14H). Physical properties of the tube (including but not limited to, flexibility, ability to fuse, ability to branch, etc.) may relate to membrane chemical constitution, which is suggested by the observed different susceptibility of nascent tubes to different dyes.

Membrane fenestration: Some of the crescent formations merge to create fenestrations (holes) in the connective membrane. These may appear like circular windows of various diameters opening to other layers (see, e.g., FIG. 14I and FIG. 14J). The white background observed in these figures is mostly crammed with unstained, almost unrecognizable, SMS cells. These fenestrations provide access for fluids (including nutrients or signal molecules) into other histological layers. Since many tubes of the present mesh assembly appear well connected to these fenestrations (see, e.g., FIG. 14I), they may also permit easy access of fluids to the tubular mesh assembly system. In addition, they may provide depending on diameter easy access for individual cells, cell aggregates and/or cell constructs.

Figure 15A:
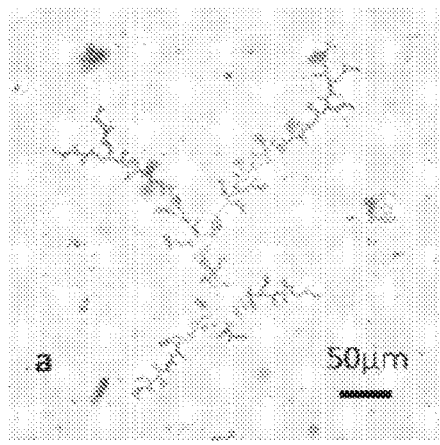
FIGS. 15A-I illustrate images of slide preparations of stained sheep heart tissues according to some embodiments. The structures are consistent with the observation in three dimensional cluster mesh assembly (FIG. 15A) in Coated tubular assembly (FIG. 15B) in two dimensional leaf mesh assembly (FIG. 15C, FIG. 15D) in Crescent formation (FIG. 15E) in membrane tube transition (FIG. 15F, FIG. 15G) and fenestrations (FIG. 15H, FIG. 15I). The images (FIGS. 15A, 15C, 15E, 15F, 15I) were taken from slide preparations stained using amido black stain, images (FIGS. 15B, 15D, 15G, 15H) were from slide preparations stained using the Masson Goldner trichrome technique.
Figure 15B:
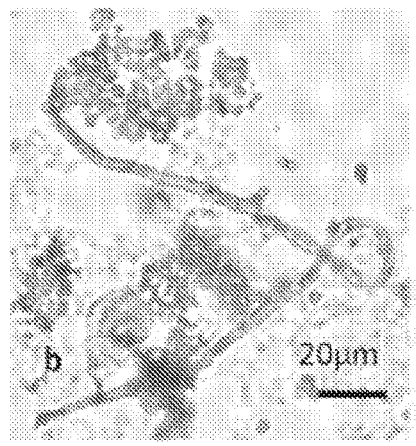
Figure 15C:
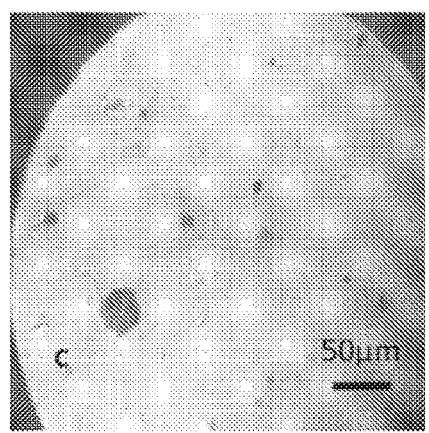
Figure 15D:
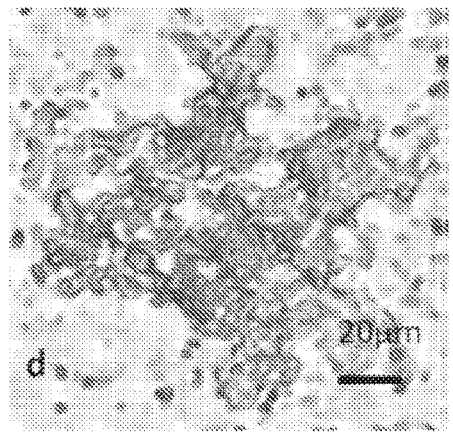
Figure 15E:
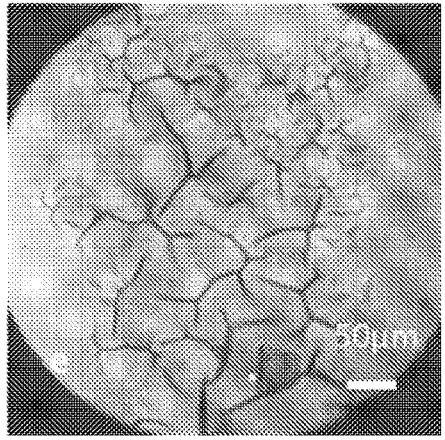
Figure 15F:
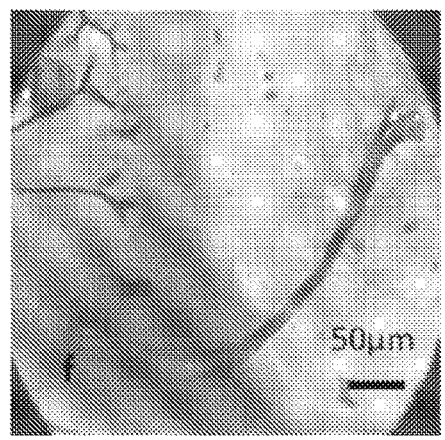
Figure 15G:
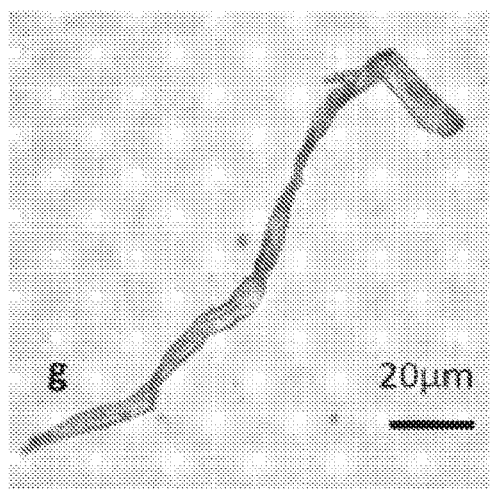
Figure 15H:
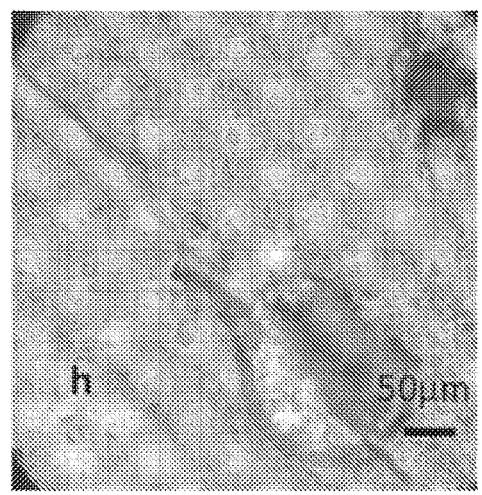
Figure 15I:
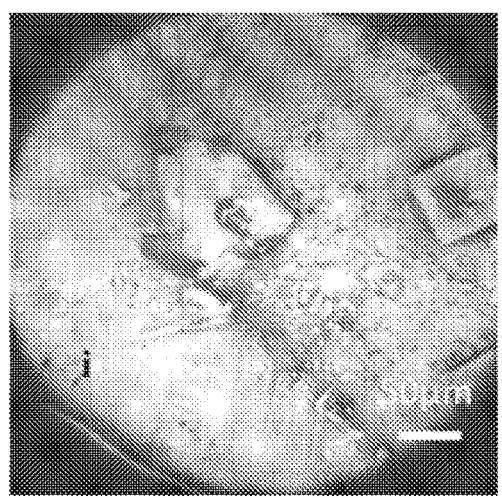
Figure 16A:
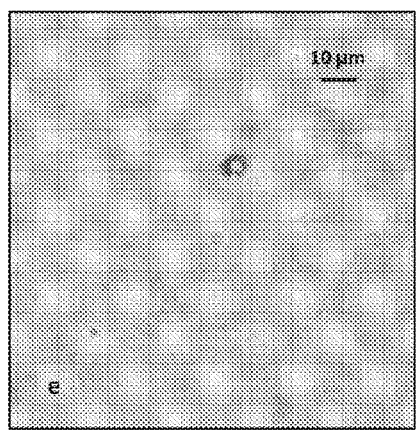
FIGS. 16A-B illustrate a white layer at the bottom (FIG. 16A) which is actually crammed with SMS cells. The image
Figure 16B:
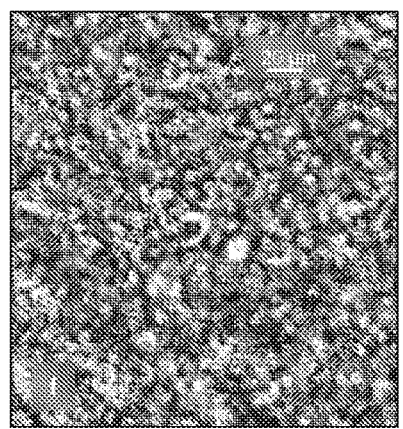
Figure 17:
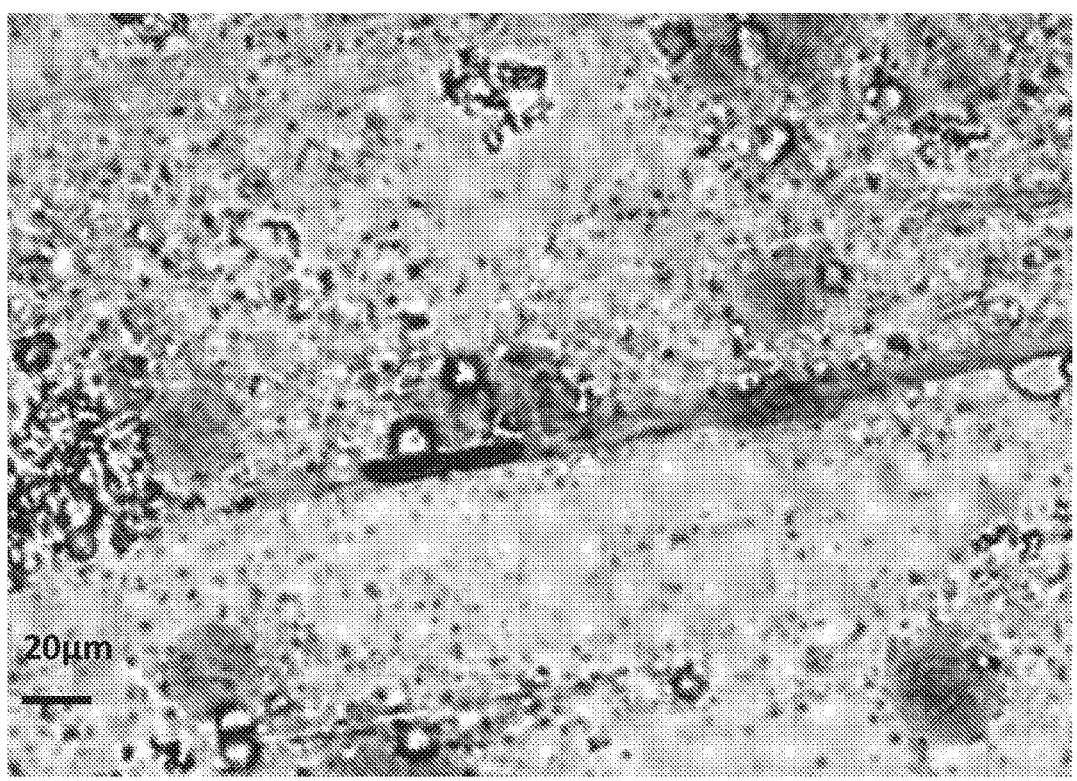
FIG. 17 illustrates amido black stained rat Cerebellum. The black dots indicate the presence of SMS cell like shaped cells in abundance.
Figure 18:
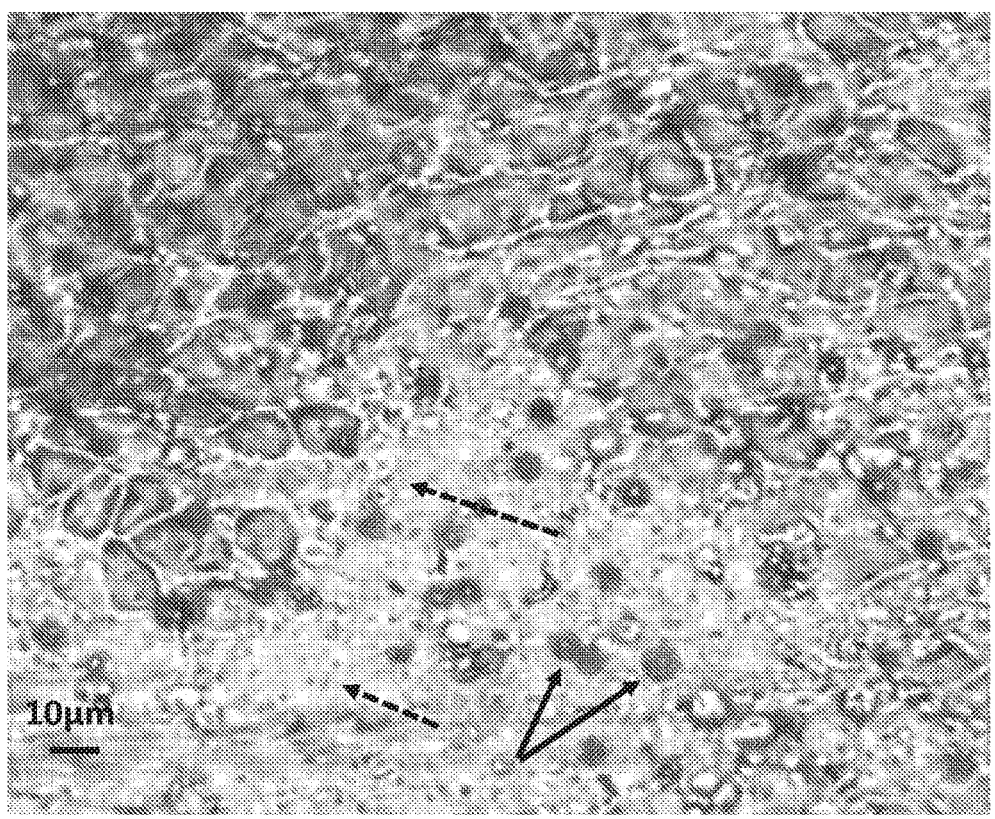
FIG. 18 illustrates Masson Goldner trichrome stained rat Cerebellum SMS cell like shaped cells appear abundant on the white background (arrow with dashes). Further cells of similar shape but that are larger and are stained appear derived from SMS cells (straight arrow).
Figure 19:
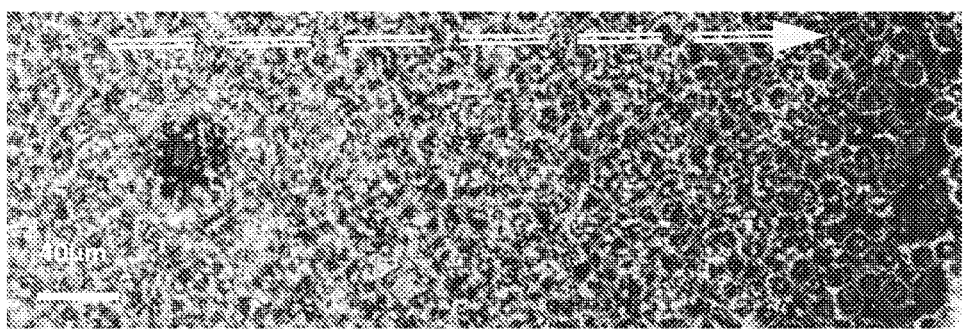
FIG. 19 illustrates amido black stained rat heart indicate the crammed presence of SMS cell like shaped cells. Cells are positionally gradually replaced by larger differentiated and stained cells (arrow). Image was subjected to digital inversion.
Figure 20A:
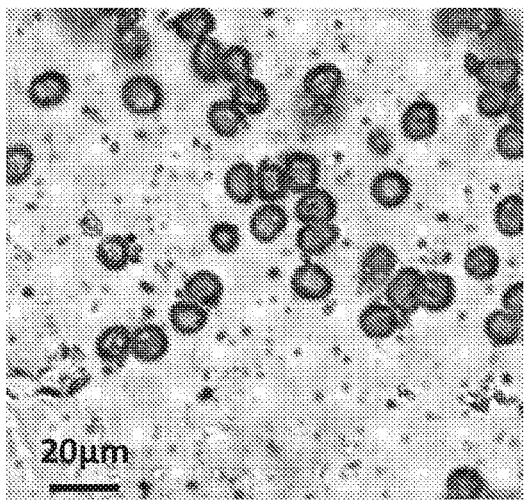
FIGS. 20A-B illustrate amido black stained rat heart indicate the presence of SMS cell-like shaped cells. Cells that are indicated by the black dots (FIG. 20A) are made more visible by subjecting image to digital inversion (FIG. 20B).
Figure 20B:
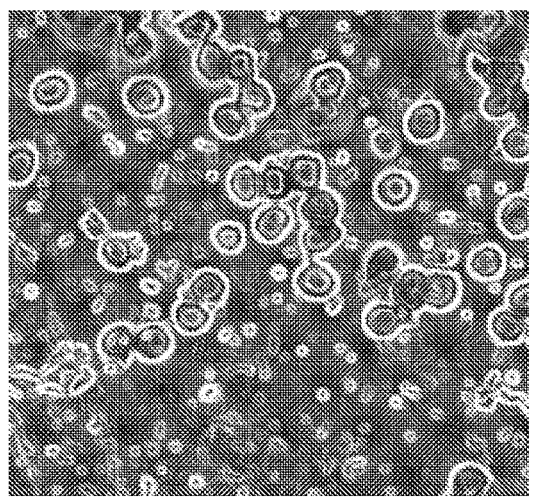
Figure 21:
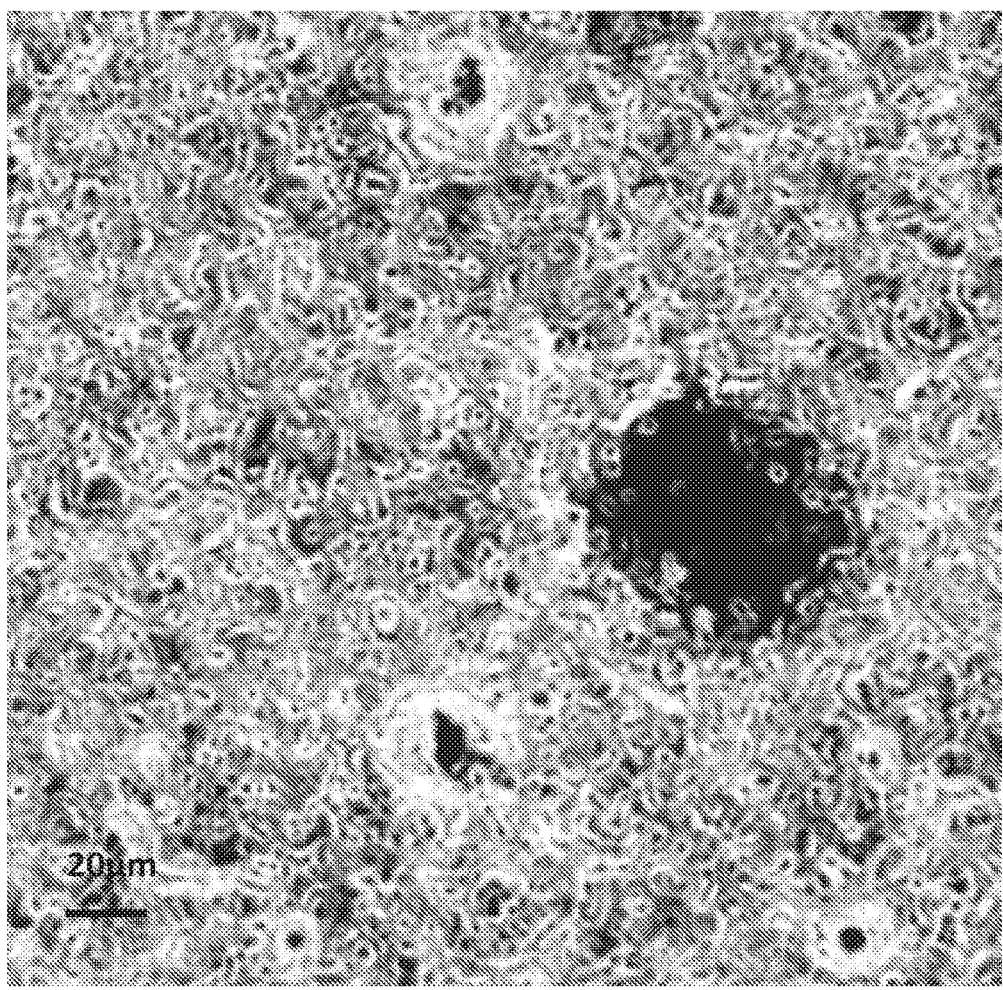
FIG. 21 illustrates amido black stained rat heart indicate the crammed presence of SMS cell like shaped cells. Image was subjected to digital inversion.
Figure 22:
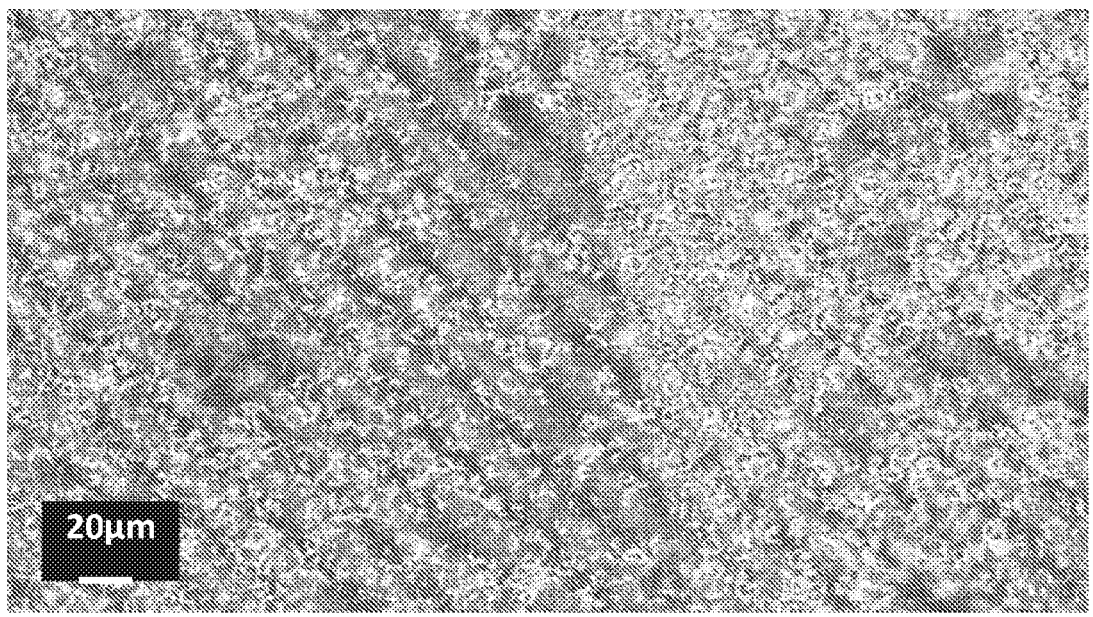
FIG. 22 illustrates Masson Goldner trichrome stained rat heart indicate the crammed presence of SMS cell like shaped cells. Some cells vary only slightly from the SMS cell shape geometry but demonstrate intensely different pigmentations or different affinities to stain.
Figure 23:
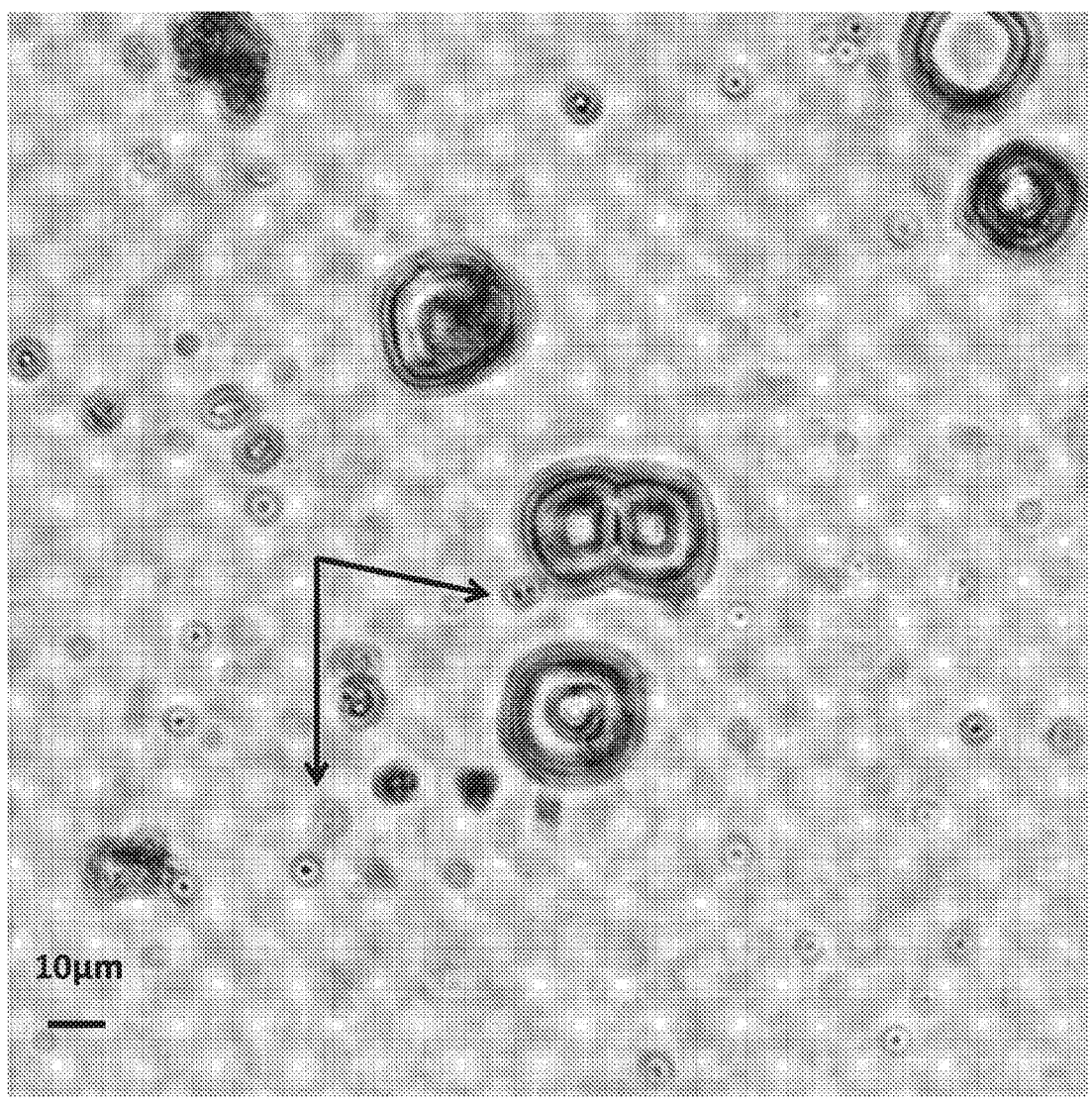
FIG. 23 illustrates Masson Goldner trichrome stained rat heart indicate the clear presence of cells with the characteristic SMS cell like shape. In this embodiment, some cells appear to be dividing.
Figure 24:
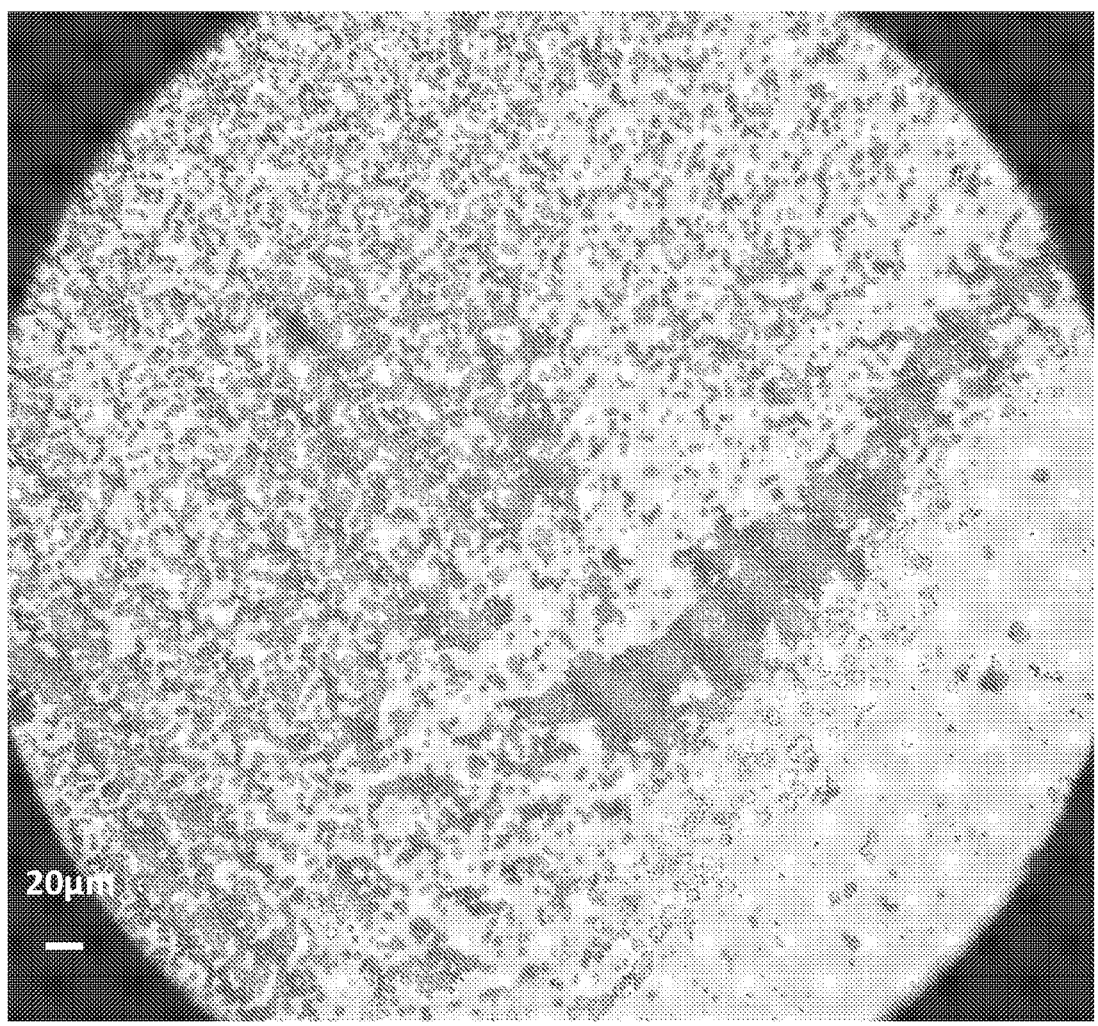
FIG. 24 illustrates Masson Goldner trichrome stained rat heart indicate the crammed presence of SMS cell like shaped cells. In this embodiment, some cells vary only slightly from the SMS cell shape geometry but demonstrate intensely different pigmentations or different affinities to stain.
Figure 25:
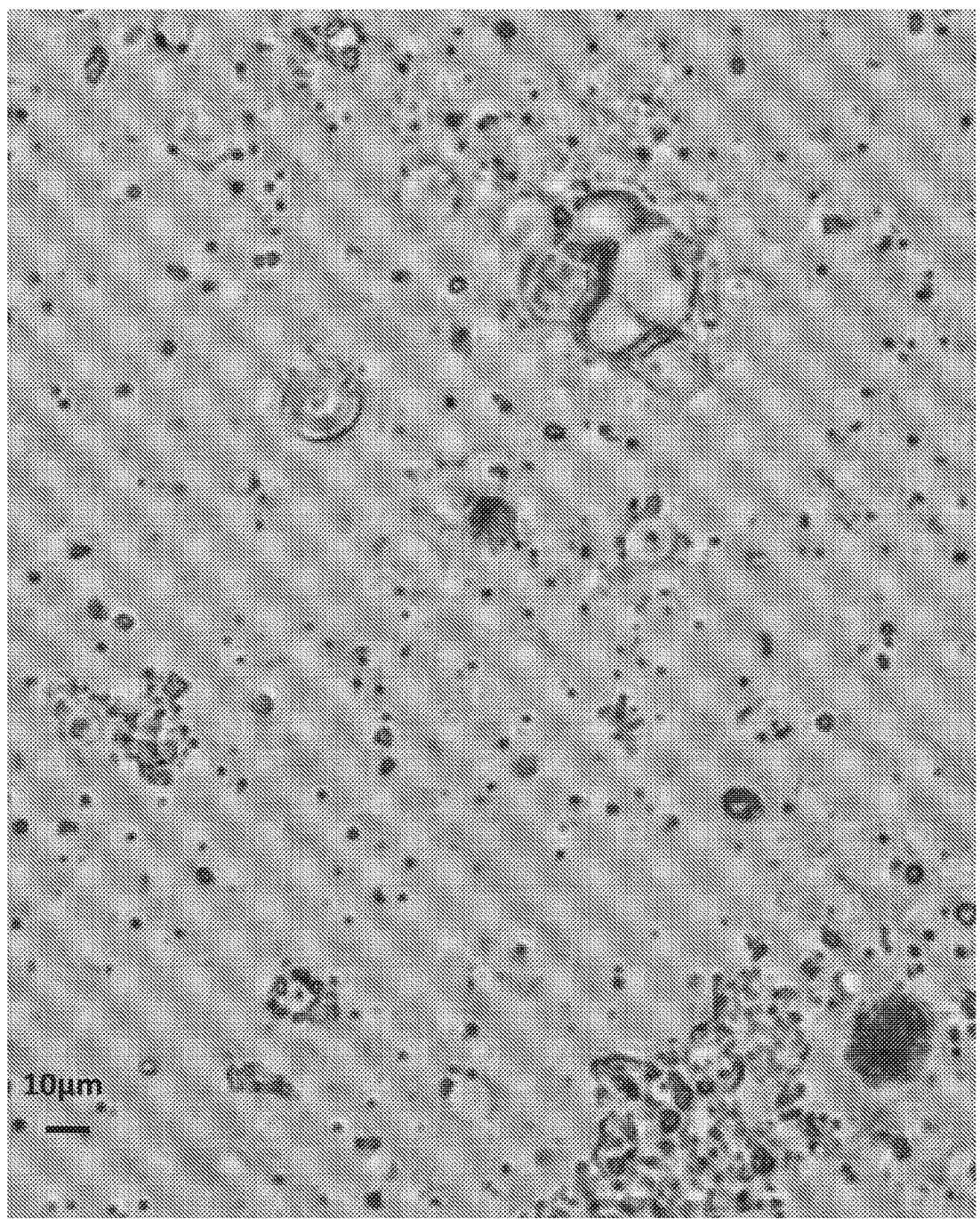
FIG. 25 illustrates Masson Goldner trichrome stained rat kidney indicate the presence of SMS cell like shaped cells.
Figure 26:
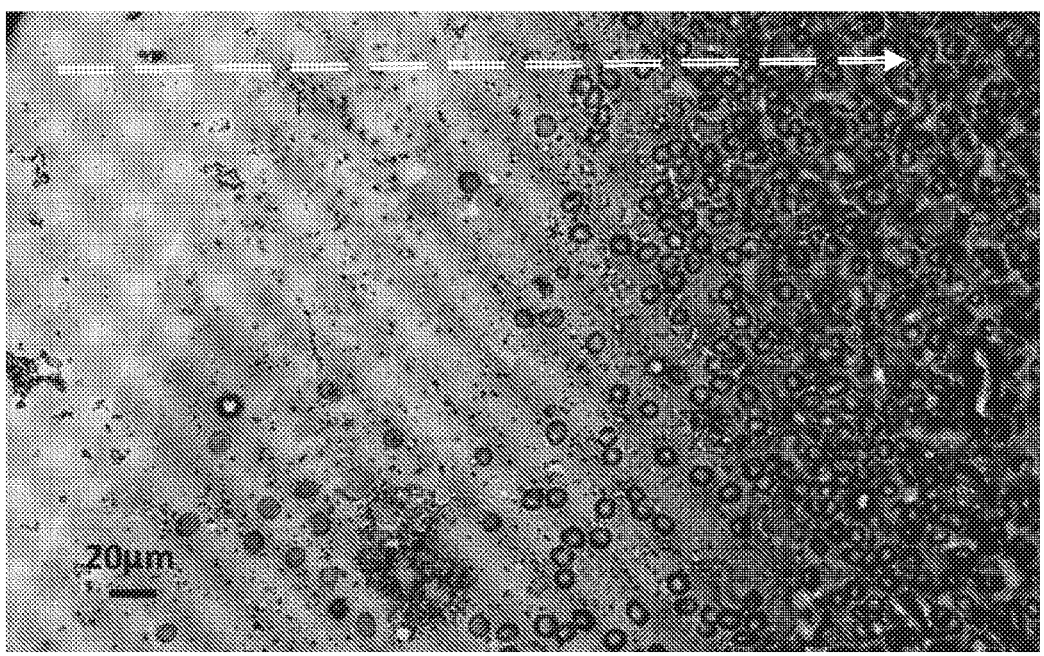
FIG. 26 illustrates amido black stained rat liver indicate the presence of SMS cell like shaped cells. Cells are positionally gradually replaced by larger differentiated and stained cells (arrow).
Figure 27:
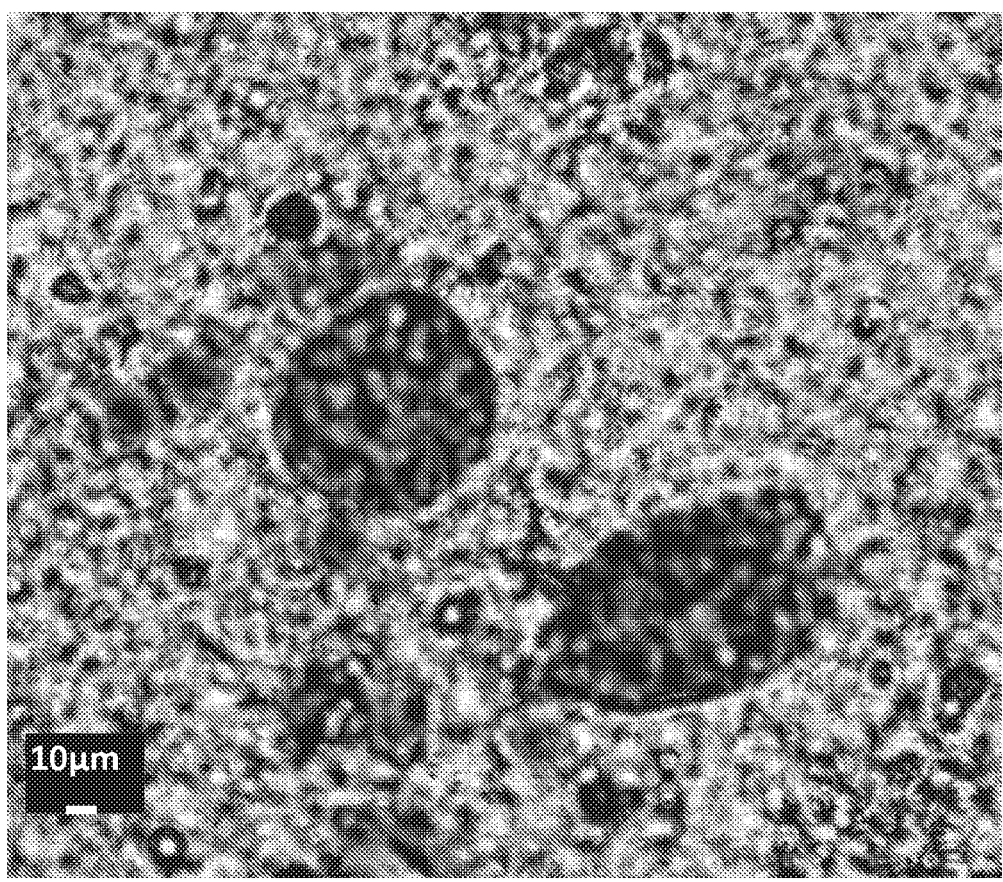
FIG. 27 illustrates amido black stained rat liver indicate the crammed presence of SMS cell like shaped cells.
Figure 28:
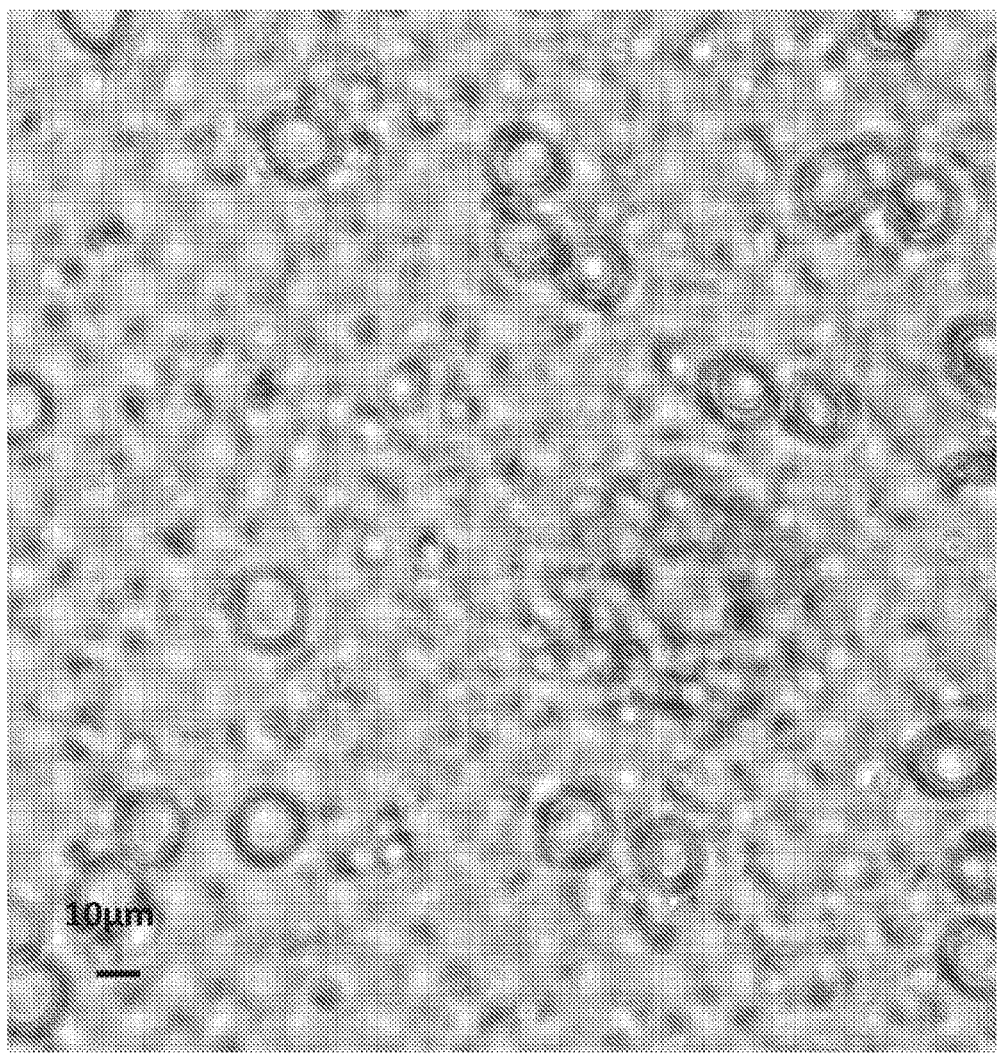
FIG. 28 illustrates Masson Goldner stained rat liver indicate the crammed presence of SMS cell like shaped cells.
Figure 29:
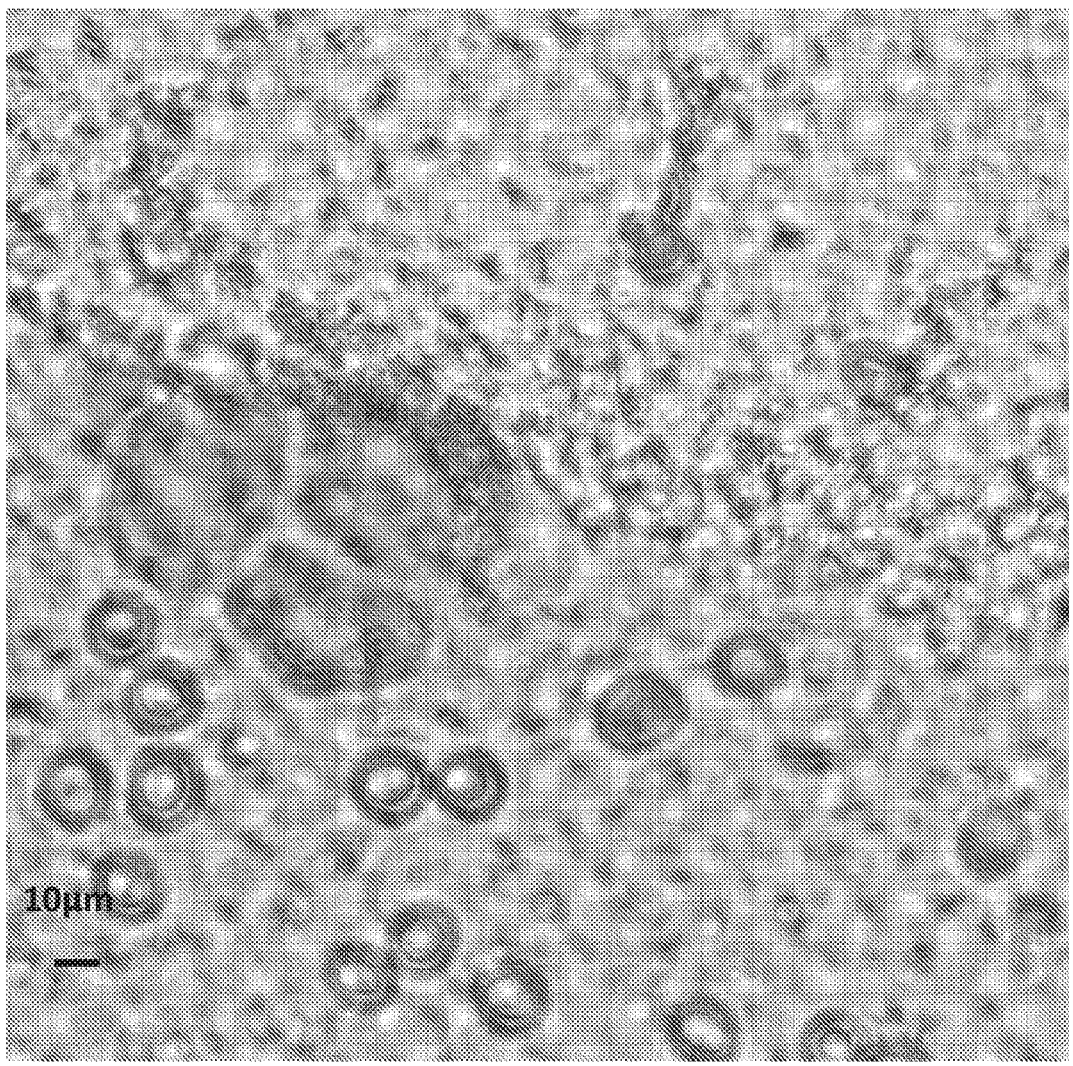
FIG. 29 illustrates Masson Goldner stained rat liver indicate the crammed presence of SMS cell like shaped cells.
Figure 30:
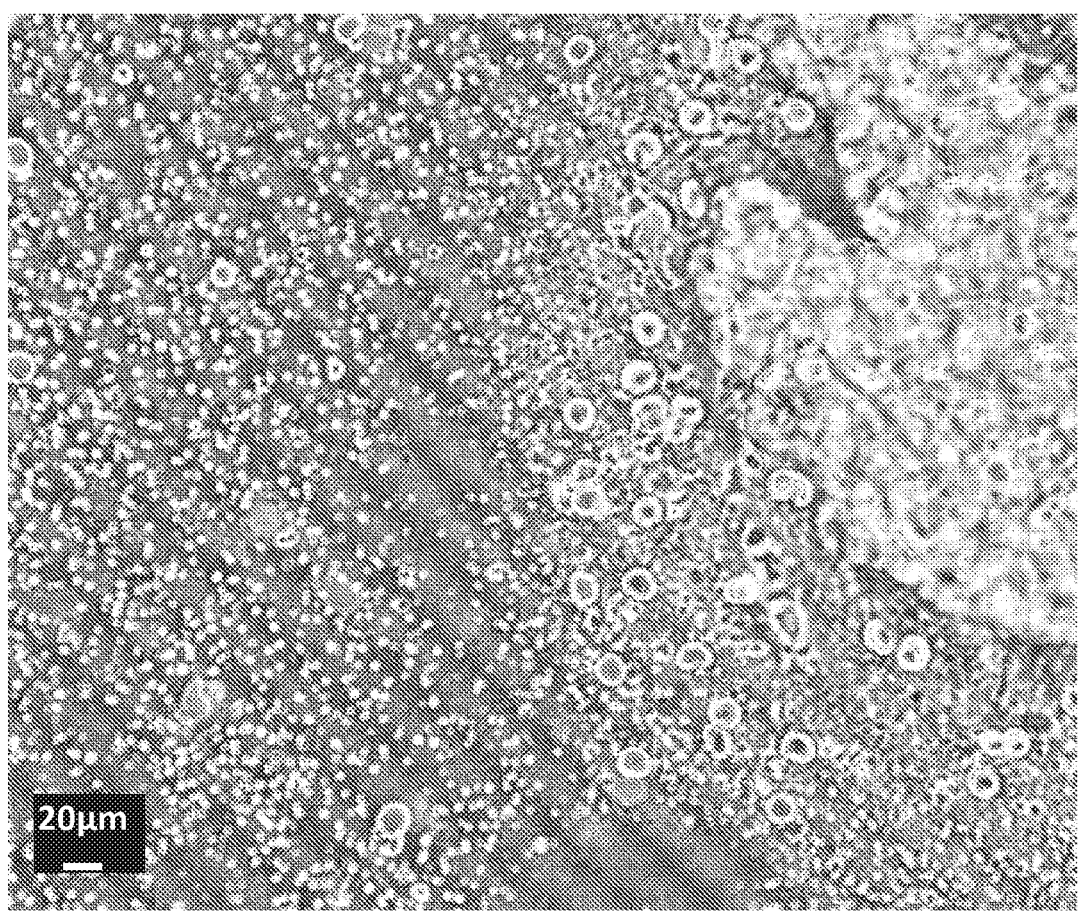
FIG. 30 illustrates Masson Goldner stained rat liver tissue indicate the crammed presence of SMS cell like shaped cells. Image was subjected to digital inversion.
Figure 31A:
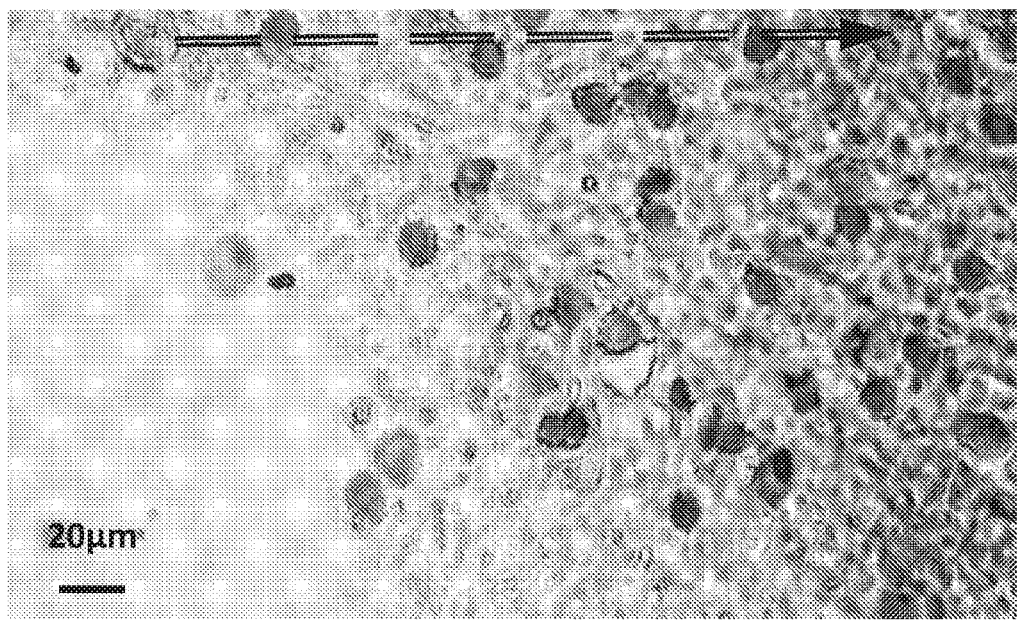
FIGS. 31A-B illustrate toluidine blue stained sheep cerebellum tissue indicate the crammed presence of SMS cell like shaped cells. Cells are positionally gradually replaced by larger differentiated and stained cells (arrow) (FIG. 31A). Image of FIG. 31A was subjected to digital inversion for better distinction of SMS cell like shaped cells (FIG. 31B).
Figure 31B:
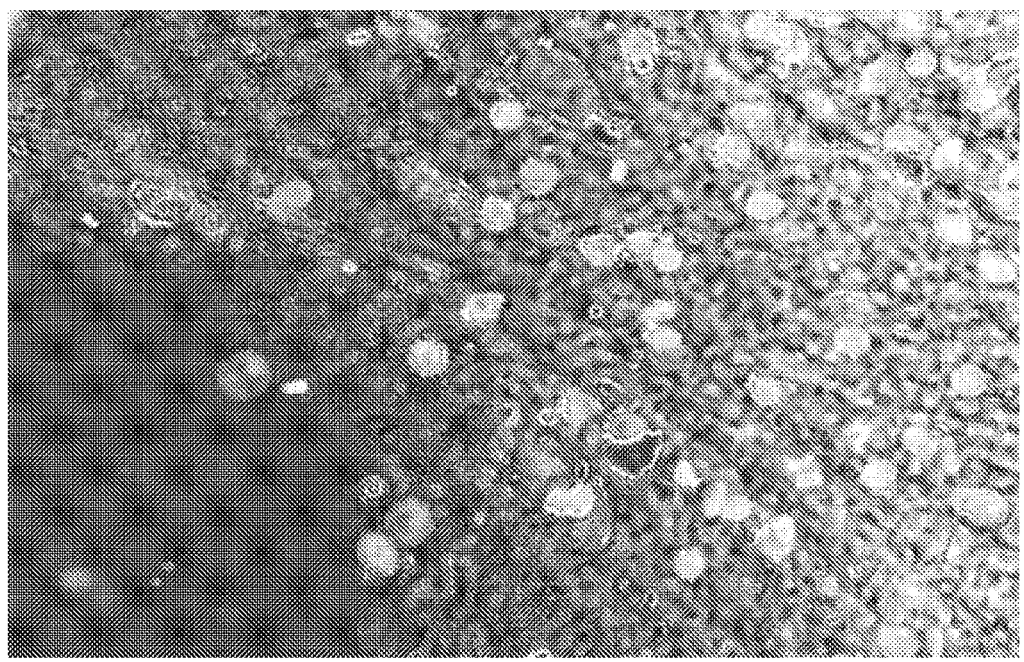
Figure 32:
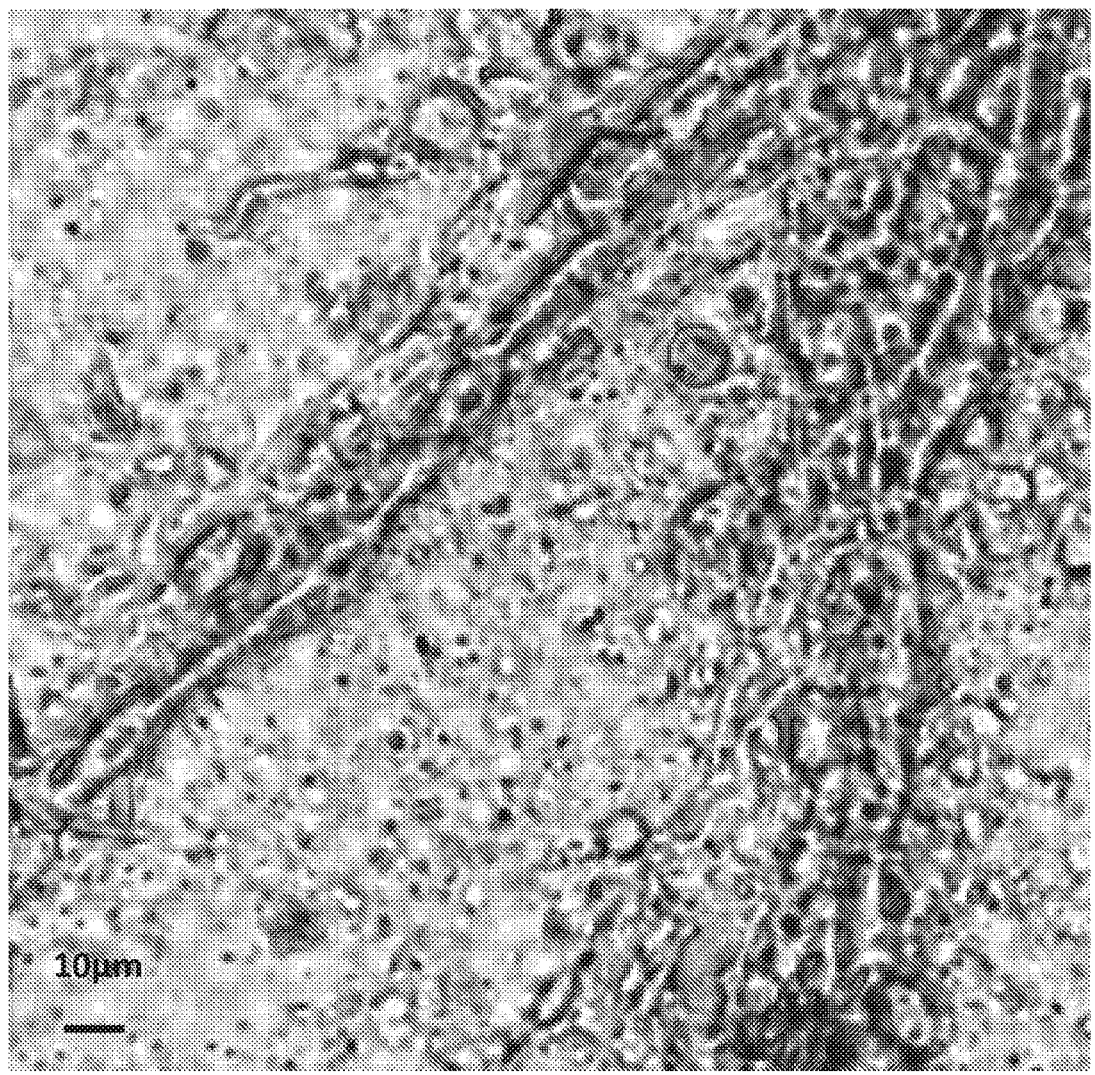
FIG. 32 illustrates toluidine blue stained sheep cerebellum tissue indicate the presence of SMS cell like shaped cells.
Figure 33:
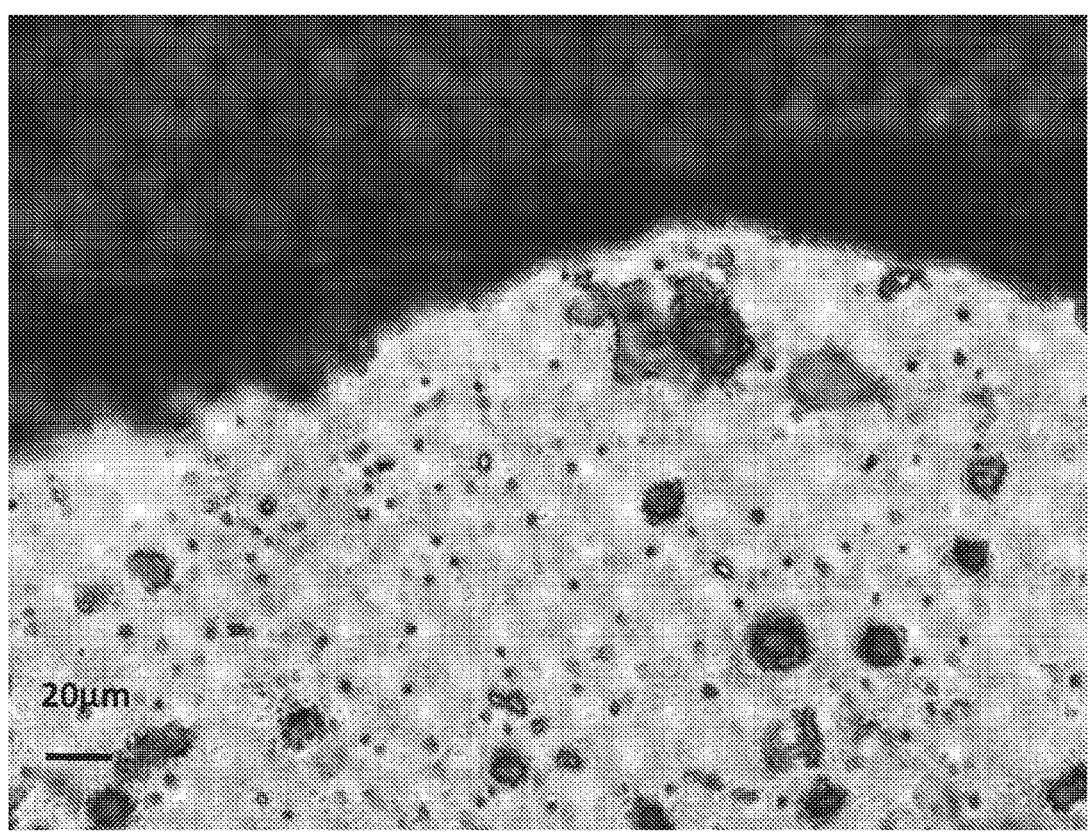
FIG. 33 illustrates amido black stained sheep heart tissue indicate the crammed presence of SMS cell like shaped cells.
Figure 34:
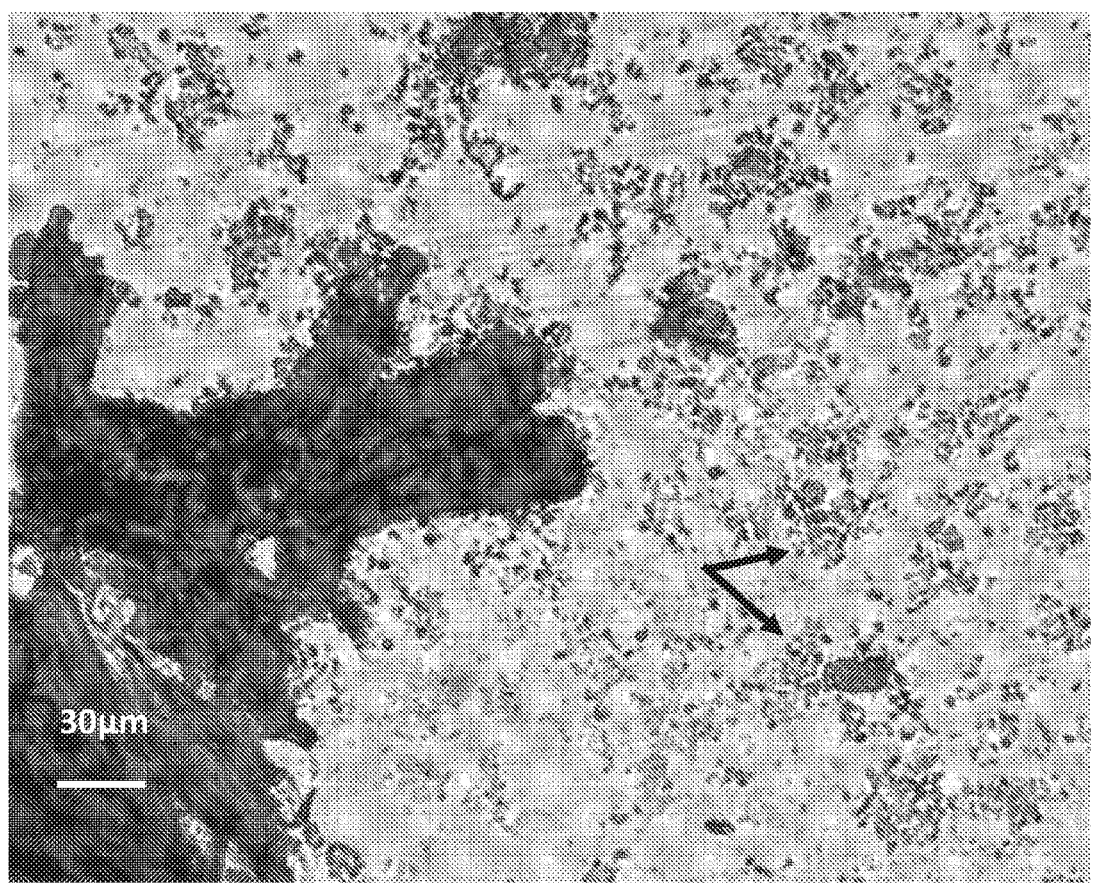
FIG. 34 illustrates Masson Goldner trichrome stained sheep heart tissue indicate the presence of SMS cell like shaped cells. Aggregated cells producing extracellular matrix appearing identical the one produced by SMS cells in vitro (arrows) (see, FIG. 13H, FIG. 13I from SMS cell culture).
Figure 35:
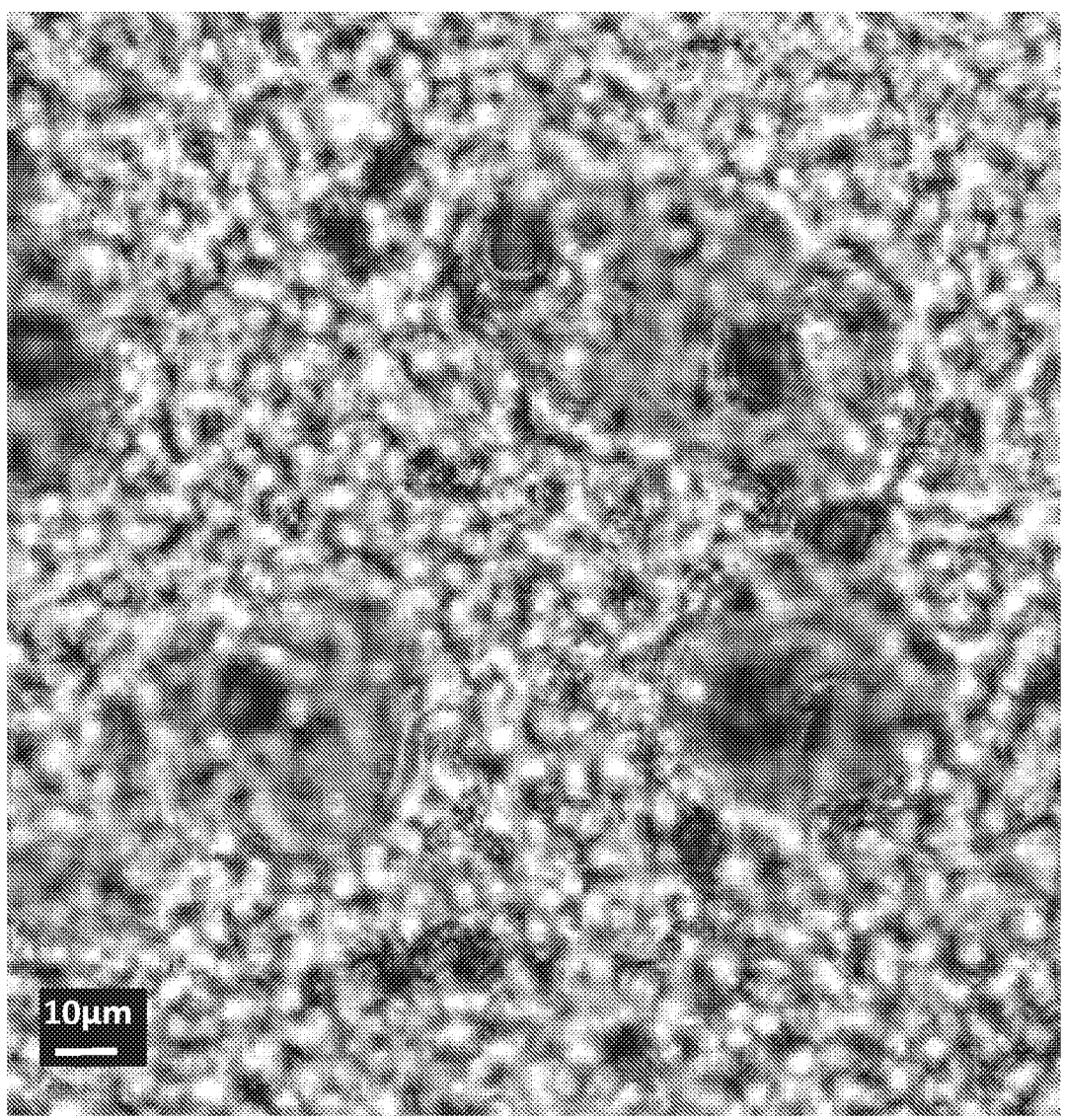
FIG. 35 illustrates Masson Goldner trichrome stained sheep liver indicate the crammed presence of SMS cell like shaped cells.
Figure 36:
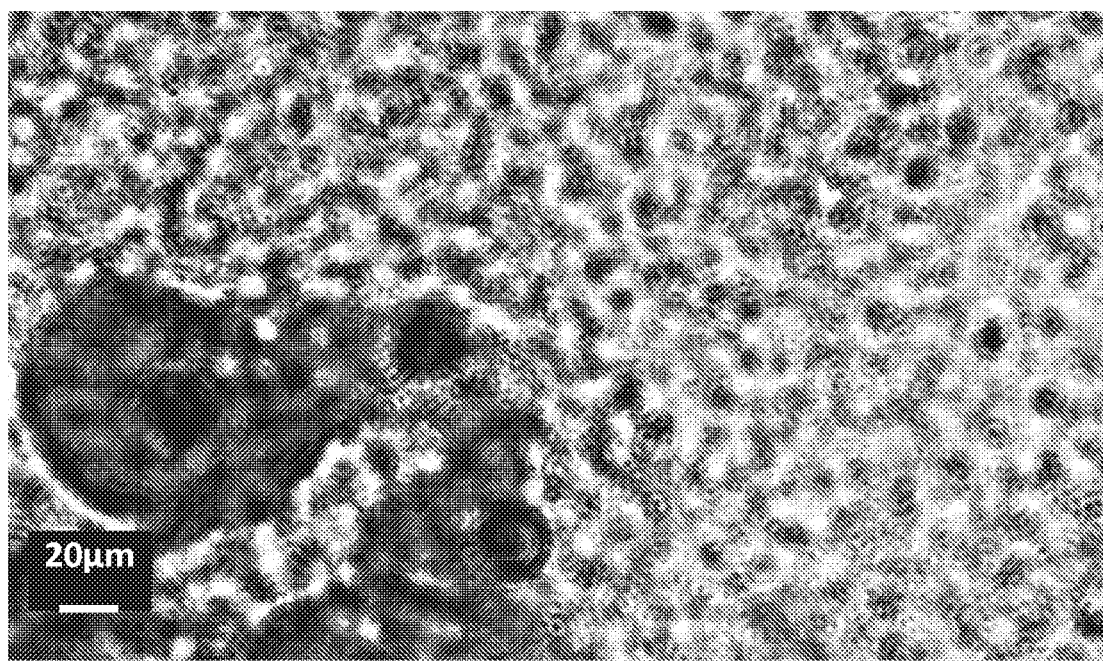
FIG. 36 illustrates Masson Goldner trichrome stained sheep liver indicate the crammed presence of SMS cell like shaped cells.
Figure 37:
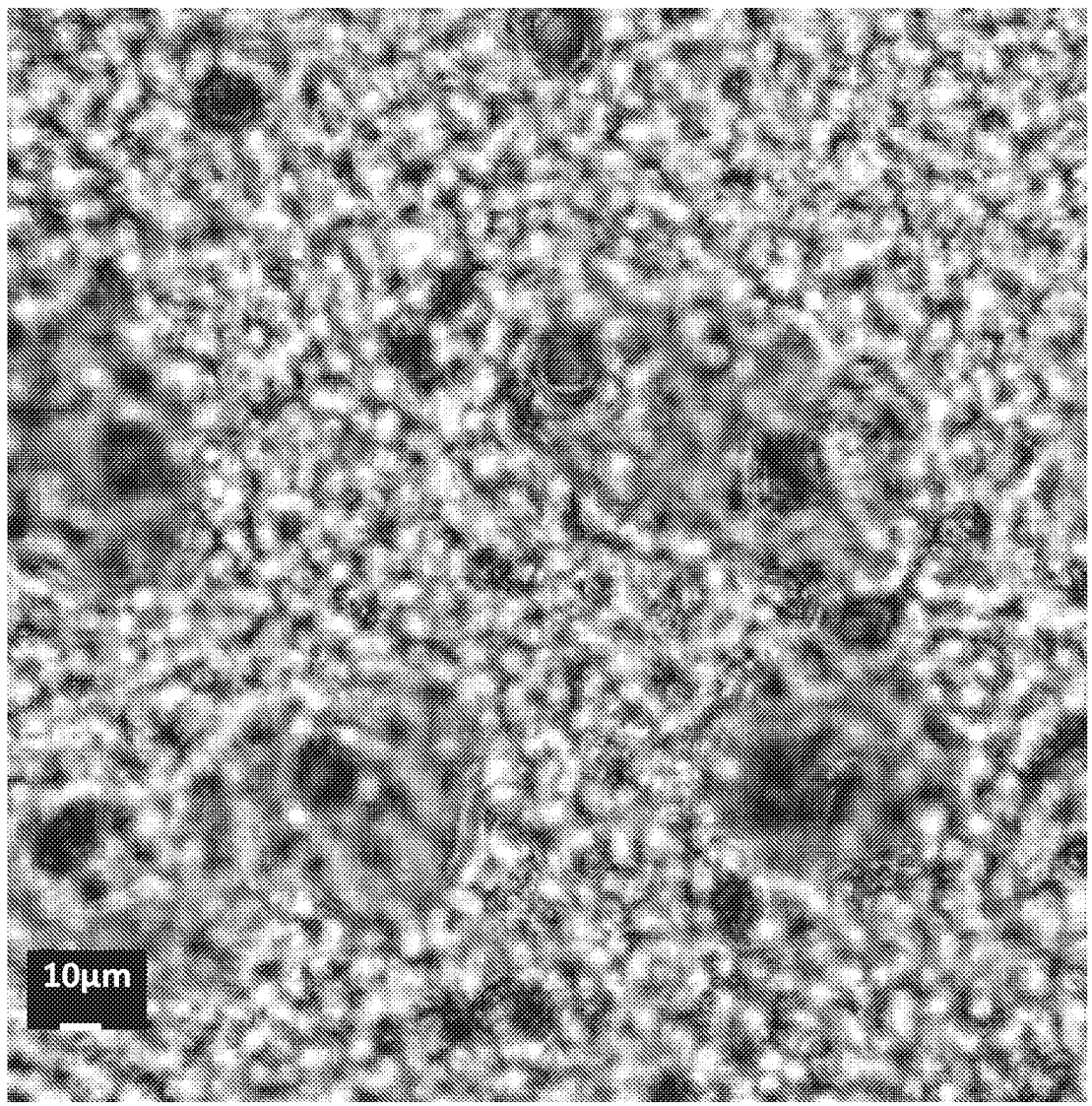
FIG. 37 illustrates Masson Goldner trichrome stained sheep liver indicate the crammed presence of SMS cell like shaped cells.
Figure 38:
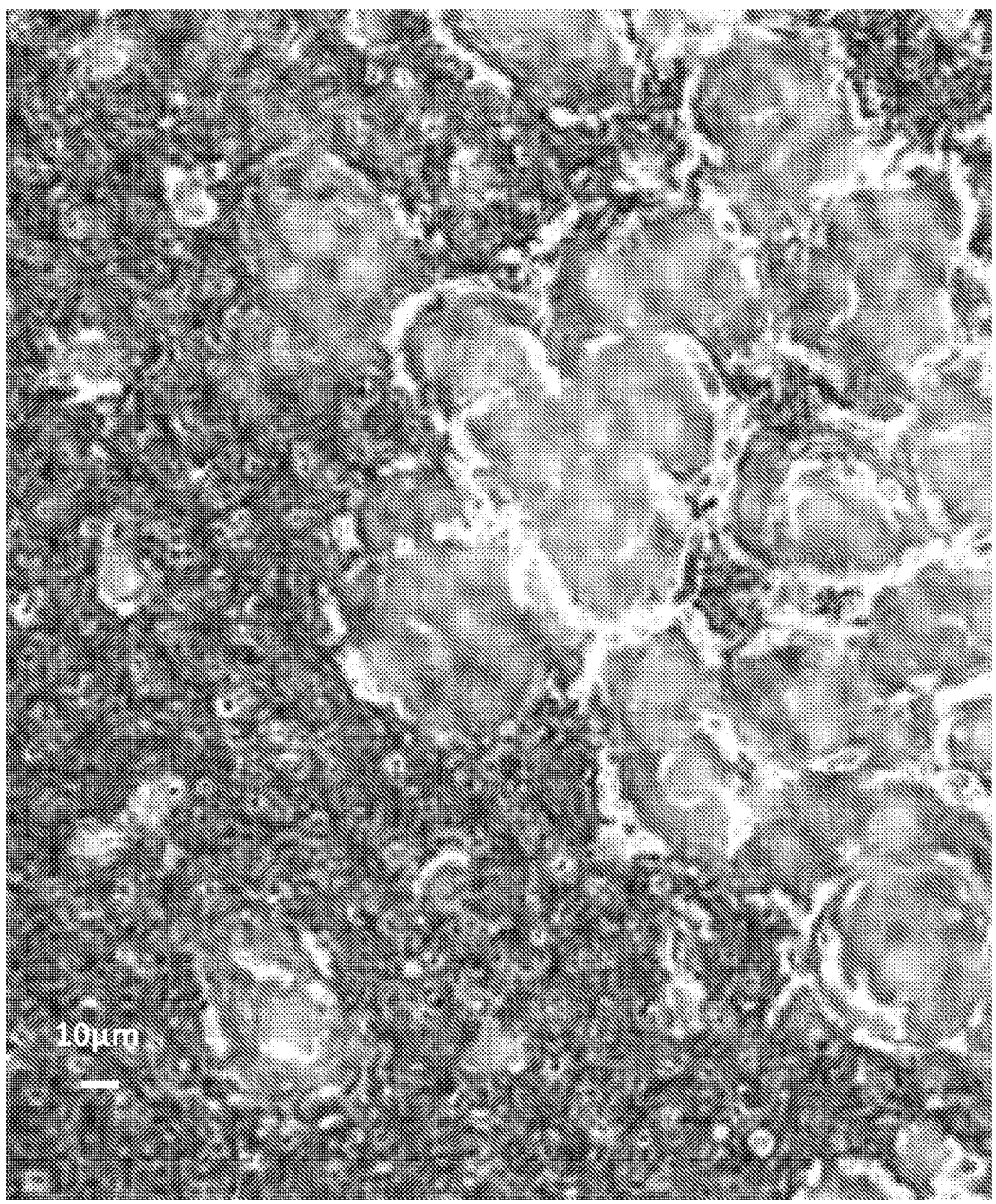
FIG. 38 illustrates Toluidine blue stained sheep liver indicate the crammed presence of SMS cell like shaped cells.
Figure 39:
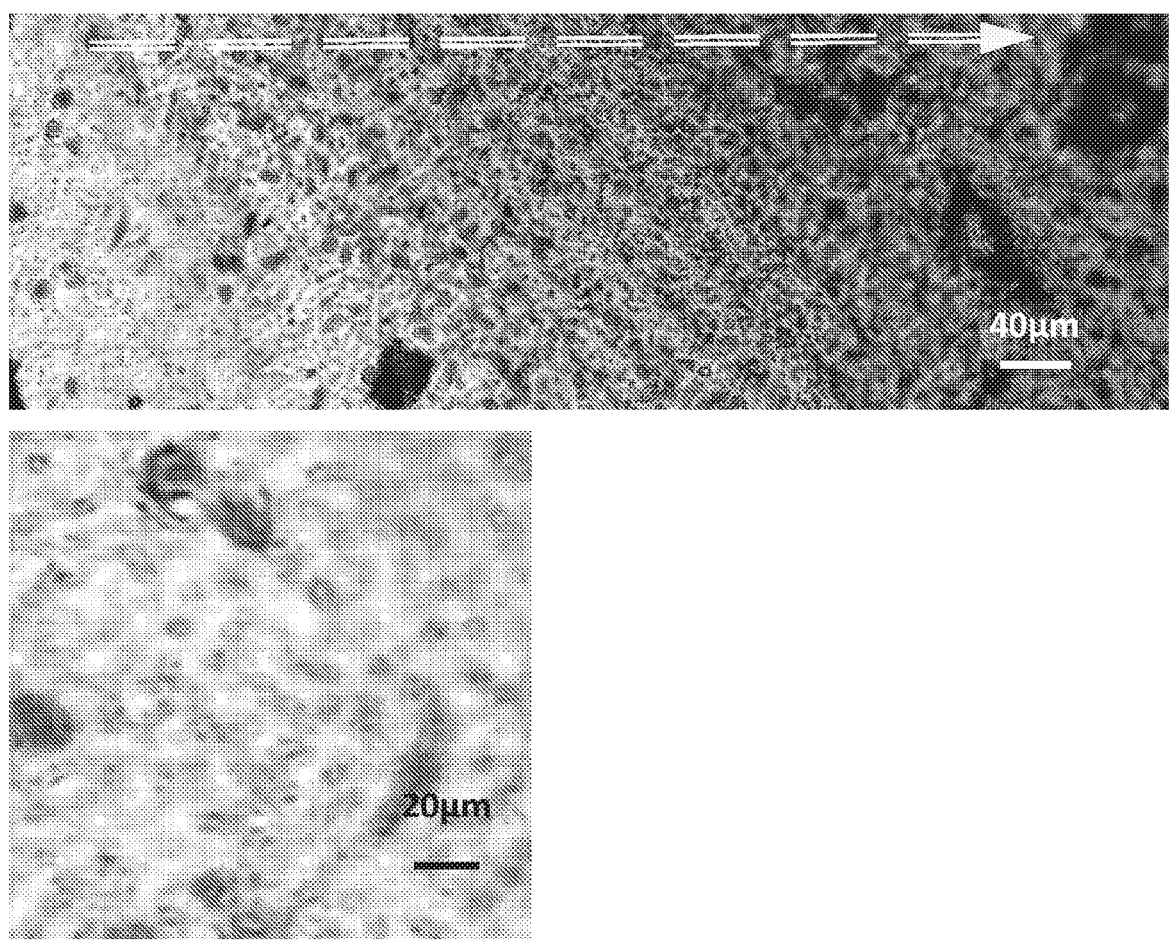
FIG. 39 illustrates Masson Goldner trichrome stained sheep kidney indicate the crammed presence of SMS cell like shaped cells. Cells are positionally gradually replaced by larger differentiated and stained cells (arrow).

Comparison of observed structures with sheep heart tissue: The structure in FIG. 15A is consistent with the one observed in three dimensional cluster mesh assembly in cell culture (see, e.g., FIG. 9H). In FIG. 15B, the structure is similar to intermediary step of the coated tubular assembly. Two dimensional leaf mesh assembly stained using Amido black is observed in FIG. 15C and related structures stained with Masson Goldner trichrome in FIG. 15D. Clearly observed in stained preparation are also: crescent formation (see, e.g., FIG. 15E) Membrane Tube transition (see, e.g., FIG. 15F, FIG. 15G). Fenestrations are also obvious (see, e.g., FIG. 15H) but may take at times different shapes than the one produced in SMS cell culture (see, e.g., FIG. 15I).

Example 6: Screening Sheep/Rat Tissues for Cells with Characteristic SMS Cell Shape Screening various tissues from sheep and rat organs indicated the abundant presence of cells that have the exceptional characteristic shape of SMS cells (see, FIGS. 17 to 39). Microscopic examination using histochemical staining demonstrate also the presence of the tissue like structure observed in the in Vitro SMS cell culture (see, FIG. 19, FIG. 21, FIG. 34). Several obtained microscopic pictures of various stained tissues suggest farther a continuum in the process of differentiation, from the small simple SMS cell type to other type differentiated cells (see, FIG. 22, FIG. 24, FIG. 34). This is suggested by a gradual shift, from the typical characteristic morphology of SMS cells, to other diverse cellular forms (see, FIG. 19, FIG. 26, FIG. 31, FIG. 39).

Example 7: Neuronal Antigens in Differentiated SMS Cells

Figure 40:
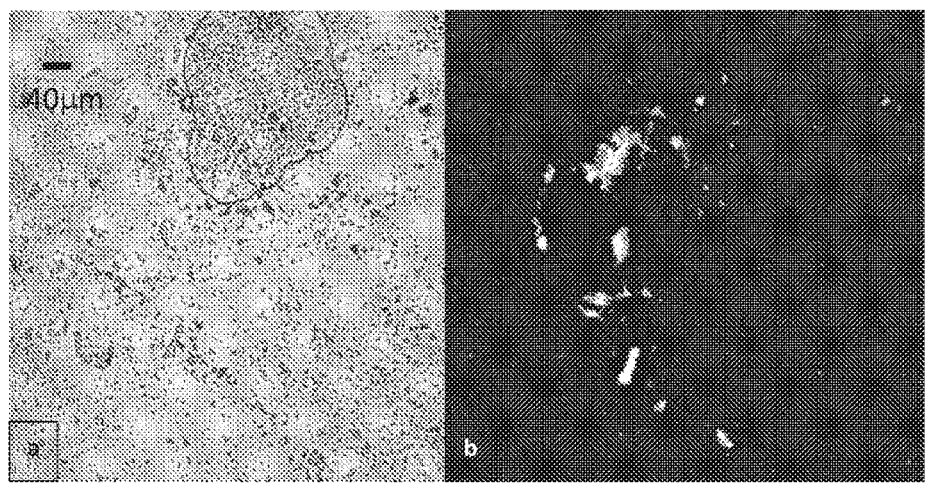
FIG. 40 illustrates the detection of the neuron specific antigen beta tubulin using antigen specific antibody in SMS cells subjected to in vitro neuronal differentiation.
Figure 41:
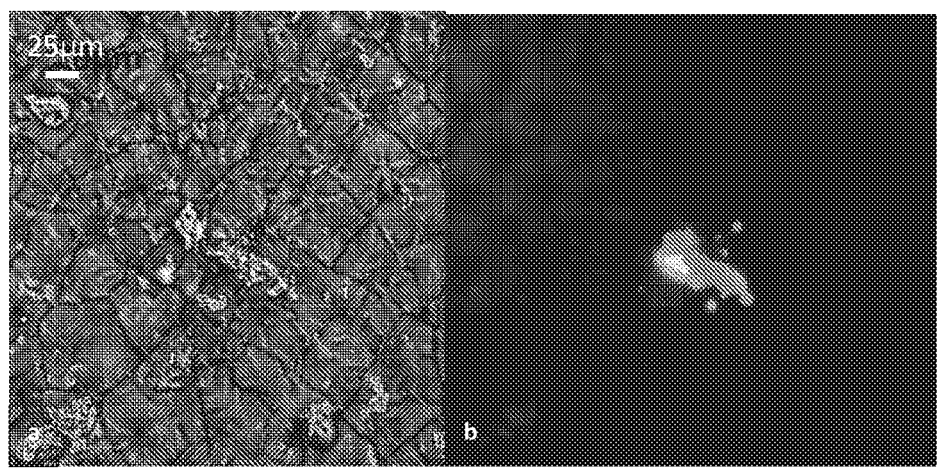
FIG. 41 illustrates the detection of the neuronal cells specific antigen GF AP using antigen specific antibody in SMS cells subjected to in vitro neuronal differentiation. Image (a) was subjected to enhancement and digital inversion.
Figure 42:
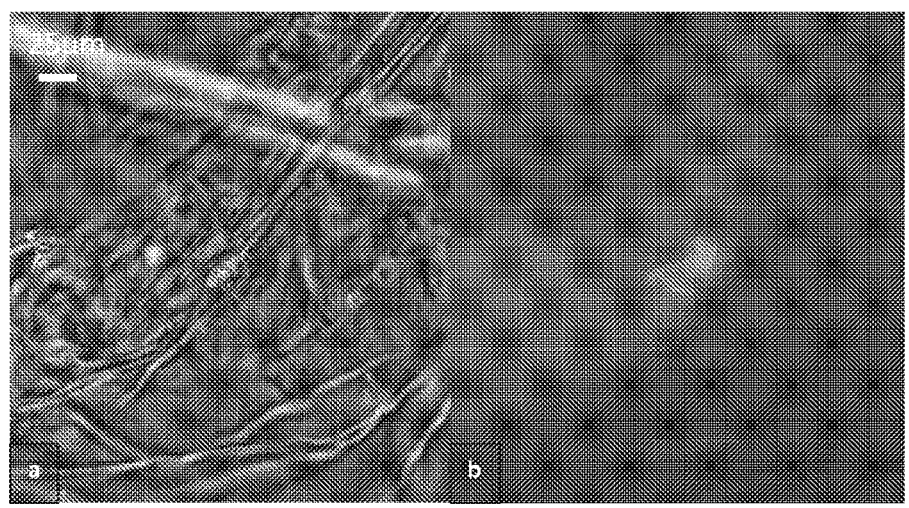
FIG. 42 illustrates the detection of the neuronal cells specific antigen PLP using antigen specific antibody in SMS cells subjected to in vitro neuronal differentiation.

Cells obtained by in vitro neurogenic differentiation of cultured SMS cells were tested for various antigens that are typical to neuronal cells. Testing using antigen specific fluorescent antibodies resulted in positive signals for the three examined neuronal antigens (class III beta Tubulin, Glial fibrillary acidic protein GF AP, Myelin proteolipid protein PLP) (see, FIG. 40, FIG. 41, FIG. 42).

The above description of the disclosed embodiments to enable any person skilled in the art to make or use the invention. Various modifications to these embodiments will be readily apparent to those skilled in the art, and the generic principles described herein can be applied to other embodiments without departing from the spirit or scope of the disclosure. Thus, it is to be understood that the description and drawings presented herein represent an exemplary embodiment of the disclosure and are therefore representative of the subject matter which is broadly contemplated by the present invention. It is further understood that the scope of the present disclosure fully encompasses other embodiments that may become obvious to those skilled in the art and that the scope of the present disclosure is accordingly not limited.

What is claimed is:

1. A method of producing a tubule from an extracellular matrix (ECM) protein from small mobile stem (SMS) cells, comprising:
    culturing ECM obtained from a population of isolated SMS cells under conditions, which promote the formation of a tubule; and
    identifying a tubule produced in the culture, wherein the ECM is cultured in a growth media comprising a Dulbecco's Modified Eagle's medium and heat inactivated fetal bovine serum.

2. The method of claim 1, wherein the tubule is from 3 to 4 um in diameter.

3. The method of claim 1, wherein the tubule forms a three-dimensional cluster mesh assembly, a coated tubular assembly, or a two-dimensional leaf mesh assembly, or a combination thereof.

4. The method of claim 1, wherein the ECM is cultured in the presence of isolated cells enriched for a CD34 positive fraction.

5. The method of claim 1, wherein the ECM is cultured in the presence of isolated SMS cells.

* * * * *